Figure 1:
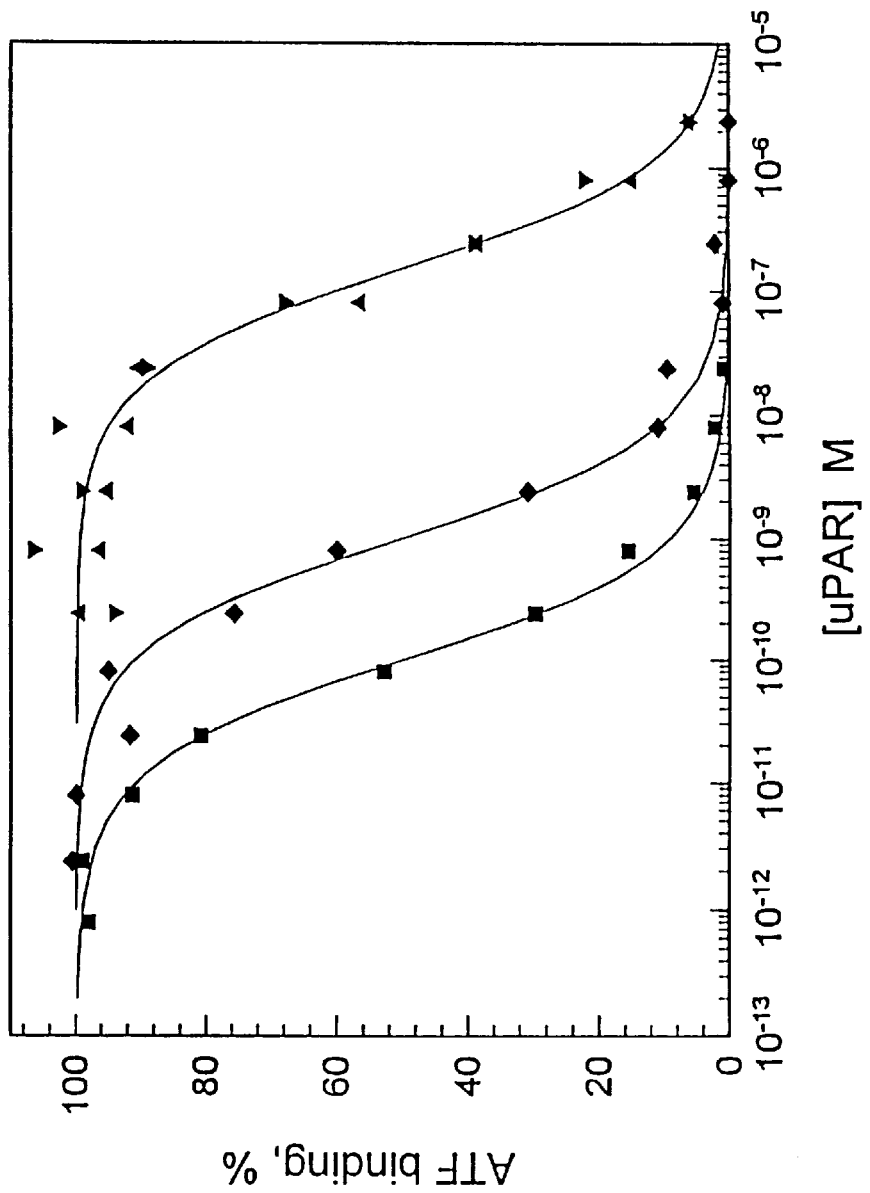

US006025142A

United States Patent [19]
Pessara et al.

[11] Patent Number: 6,025,142
[45] Date of Patent: Feb. 15, 2000

[54] HYDROPHOBIC U-PAR BINDING SITE

[75] Inventors: Ulrich Pessara, Penzberg; Ulrich Weidle, München; Bernhard König, Berg; Ulrich Kohnert, Habach; Ilse Bartke, Bernried, all of Germany; Keld Danø, Charlottenlund; Michael Ploug, Copenhagen, both of Denmark; Vincent Ellis, Woodford Green, United Kingdom

[73] Assignees: Boehringer Mannheim GmbH, Mannheim, Germany; Cancerforskningsfonden af 1989, Copenhagen K, Denmark

[21] Appl. No.: 08/458,585

[22] Filed: Jun. 2, 1995

[30] Foreign Application Priority Data

Jul. 8, 1994 [DK] Denmark ................................. 0831/94

[51] Int. Cl.[7] ............................ G01N 33/53; C07K 16/00
[52] U.S. Cl. ........................ 435/7.1; 435/7.9; 530/387.3; 530/388.15; 530/388.22; 530/388.25; 530/389.3; 530/389.7; 530/387.9
[58] Field of Search .................................... 424/9.1, 9.34, 424/9.341, 133.1–136.1, 139.1, 146.1, 143.1, 141.1, 145.1, 158.1, 174.1, 800, 809; 530/387.3, 389.9, 388.15, 388.22, 388.25, 388.26, 388.8, 389.3, 389.7, 391.1, 391.3, 413, 808, 866; 435/7.21, 7.2, 7.1, 7, 23, 7.9, 7.95, 240.1, 240.26, 240.27, 972, 325, 328, 331, 334, 338; 436/518, 523–531, 547, 824, 819

[56] References Cited

U.S. PATENT DOCUMENTS 5,519,120   5/1996   Dano et al. ........................ 530/388.22

FOREIGN PATENT DOCUMENTS 9012091   10/1990   WIPO .
9207083   4/1992   WIPO .
09808   5/1993   WIPO .

OTHER PUBLICATIONS

Mohanam et al, Cancer Research vol. 53 p. 4143, Sep. 1993.
Behrendt, et al., The Ligand–binding Domain of the Cell Surface Receptor for Urokinase–type Plasminogen Activator, The Journal of Biological Chemistry, vol. 266, vno. 12, pp. 7842–7847, 1991.
Blasi, Surface Receptors for Urokinase Plasminogen Activator, Fibrinolysis, vol. 2, pp. 73–84, 1988.
Ellis, et al., The Urokinase Receptor: Involvement in Cell Surface Proteolysis and Cancer Invasion, Ann. N.Y. Acad. Sci. vol. 667, pp. 13–31, 1992.
Fleming, et al., Protein Sequence and Potential Structural Similarity to a–Bungarotoxin and Other Neurotoxin The J. Biom. Immunology, vol. 150, No. 12, pp. 5379–5390, 1993.
Fletcher, et al., Sequence–specific H–NMR assignments and folding topology of human CD59, Protein Science, vol. 2, pp. 2015–2027, 1993.
Herskovits, Difference Spectroscopy, Methods in Enzymology, vol. 11, pp. 748–775, 1967.
Isenman, et al. Nucleophilic Modification of Human Complement Protein C3: Correlation of Conformational Changes with Acquisition of C3b–like Functional Properties, Biochemistry, vol. 20, pp. 4458–4467, 1981.
Isenman, Conformational Changes Accompanying Proteolytic Cleavage of Human Complement Protein C3b by the Regulatory Enzyme Factor I and its Cofactor H, J. Biol. Chem., vol. 258, No. 7, pp. 4238–4244, 1983.
Laemmli, Cleavage of Structural Proteins during the Assembly of the Head of Bacteriophage T4, Nature, vol. 227, pp. 680–685, 1970.
Mazar, et al., Domain Analysis of Urokinase Plasminogen Activator (u–PA): Preparation and Characterization of Intact A–Chain Molecules, Fibrinolysis, vol. 6, suppl. 1, pp. 49–55, 1992.
Nielsen, et al., A 55,000–60,000 $M_r$ Receptor Protein for Urokinase–type Plasminogen Activator, J. Biol. Chem vol. 263, pp. 2358–2363, 1988.
Palfree, The urokinase–type plasminogen activator receptor is a member of the Ly–6 superfamily, Immunol. Today, vol. 12, No. 5, pp. 170–171, 1991.
Ploug, et al. Cellular Receptor for Urokinase Plasminogen Activator, J. Biol. Chem., vol. 266, pp. 1926–1936, 1991.
Ploug, et al. Protein Structure and Membrane Anchorage of the Cellular Receptor for Urokinase–Type Plasminogen Activator, Seminars in Thrombosis and Hemostasis, vol. 17, No. 3, pp. 183–193, 1991.
Ploug, et al. The Receptor for Urokinase–Type Plasminogen Activator is Deficient on Peripheral Blood Leukocytes in Patients with Paroxysmal Nocturnal Hemoglobinuria, Blood, vol. 79, No. 6, pp. 1447–1455, 1992.

(List continued on next page.)

*Primary Examiner*—Sheela Huff
*Attorney, Agent, or Firm*—Iver P. Cooper

[57] ABSTRACT

The invention relates to an antibody which inhibits the binding between u-PA and u-PAR to an extent of at least 90% in an assay as defined in the specification, or an active fragment or immunological equivalent of said antibody. Examples of such antibodies are deposited Jul. 7, 1994 at Deutsche Sammlung von Mikroorganismen und Zellkulturen (DSM) with accession numbers DSM ACC2178 and DSM ACC2179 under the terms and conditions of the Budapest Treaty. The invention furthermore relates to a method for detecting or quantifying u-PAR or a glycosylation variant of u-PAR in a sample by use of an antibody according to the invention.

Furthermore, the invention relates to a method for the manufacture of a therapeutic agent for preventing or counteracting localized proteolytic activity using of an antibody of the invention as well as to use of an antibody according to the invention for the preparation of a diagnostic agent which is capable of targeting a diagnostic to a cell that contains a u-PAR on the surface.

11 Claims, 6 Drawing Sheets

OTHER PUBLICATIONS

Ploug, et al. Localization of the Disulfide Bonds in the $NH_2$–terminal Domain of the Cellular Receptor for Human Urokinase–type Plasminogen Activator, The J. Biol. Chem., vol. 268, No. 23, pp. 17539–17546, Aug. 15, 1993.

Pyke, et al. Urokinase–type Plasminogen Activator is Expressed in Stromal Cells and its Receptor in Cancer Cells at Invasive Foci in Human Colon Adenocarcinomas, Am. J. Pathol., vol. 138, No. 5, pp. 1059–1067, May, 1991.

Roldan, et al. Cloning and expression of the receptor for human urokinase plasminogen activator, a central molecule in cell surface, plasmin dependent proteolysis, The Embo Journal, vol. 9, No. 2, pp. 467–474, 1990.

Romer, et al. The Receptor for Urokinase–type Plasminogen Activator is Expressed by Keratinocytes at the Leading Edge During Re–Epithelialization of Mouse Skin Wounds, J. Invest. Dermatol., vol. 102, No. 4, pp. 519–522, Apr. 1994.

Ronne, et al. Cell–induced potentiation of the plasminogen activation system is abolished by a monoclonal antibody that recognizes the $NH_2$ –terminal domain of the urokinase receptor, FEBS, vol. 288, No. 1, pp. 233–236, Aug. 1991.

Ronne, et al., Quantitation of the receptor for urokinase plasminogen activator by enzyme–linked immunosorbent assay, J. of Immunol Methods, vol. 167, pp. 91–101, 1994.

Stryer, L., The Interaction of a Naphthalene Dye With Apomyoglobin and Apohemoglobin, J. Mol. Biol., vol. 13, pp. 482–495, 1965.

Vassalli, et al., A Cellular Binding Site for the $M_2$ 55,000 Form of the Human Plasminogen Activator, Urokinase, J. Cell. Biol., vol. 100, pp. 86–92, Jan. 1985.

Andreasen, et al., Urokinase–Type Plasminogen Activator is Increased in the Involving Ventral Prostate of Castrated Rats, Endocrinology, vol. 126, No. 5, pp. 2567–2576, 1990.

Angerer, et al. In Situ Hybridization with RNA Probes: An Annotated Recipe, Applications to Neurobiology Oxford University Press, Oxford, pp. 71–96 (1990).

Appella, et al., The Receptor–binding Sequence of Urokinase, J. Biol. Chem., vol. 262, No. 10, pp. 4437–4440, Apr. 5, 1987.

Behrendt, et al., The Human Receptor for Urokinase Plasminogen Activator, J. Biol. Chem, vol. 265, No. 11, pp. 6453–6460, Apr. 15, 1990.

Blasi, et al., Urokinase–Type Plasminogen Activator: Proenzyme, Receptor, and Inhibitors, J. Cell. Biol., vol. 104, pp. 801–804, Apr. 1987.

Cubellis, et al., Binding of Single–chain Prourokinase to the Urokinase Receptor of Human U937 Cells, J. Biol. Chem., vol. 261, No. 34, pp. 15819–15822, Dec. 5, 1986.

Cubellis, et al., Accessibility of Receptor–Bound Urokinase to type–1 Plasminogen Activator Inhibitor, Proc. Natl. Acad., vol. 86, pp. 4828–4832, Jul. 1989.

Dano, et al., Plasminogen Activators, Tissue Degradation, and Cancer, Adv. Cancer Res., vol. 44, pp. 139–266, 1985.

Dano, et al., Plasminogen Activators and Neoplasia, Physiological and Clinical Aspects, C. Kluft Ed., CRC Press, Boca Raton, vol. 1, pp. 19–46, 1988.

Dano, et al., The Urokinase Receptor and Regulation of Pericellular Plasminogen Activation, Molecular Biology of the Cardiovascular, vol. 132, pp. 173–186, 1990.

Hansen, et al., Sensitive and specific enzyme–liked immunosorbent assay for urokinase–type plasminogen activator and its application to plasma from patients with breast cancer, J. Lab. Clin. Med., vol. 111, pp. 42–51, 1988.

Skriver, et al., Immunocytochemical Localization of Urokinase–type Plasminogen Activator in Lewis Lung Carcinoma, J. Cell Biology, vol. 99, pp. 753–758, Aug. 1984.

Ploug, et al., Ligand Interaction between Urokinase–Type Plasminogen Activator and its Receptor Probed with 8–Anilino–1–napthalenesulfonate. Evidence for a Hydrophobic Binding Site Exposed Only on the Intact Receptor, Biochemistry, vol. 33, No. 30, pp. 8991–8997, 1994.

HYDROPHOBIC U-PAR BINDING SITE

FIELD OF THE INVENTION

The present invention relates to further developments, improvements and refinements of the inventions disclosed in WO 90/12091 and WO 92/07083.

GENERAL BACKGROUND

According to the literature, urokinase-type plasminogen activator (u-PA) has been found in all mammalian species so far investigated. Several findings relate u-PA to tissue degradation and/or cell migration, presumably through a breakdown of the extracellular matrix, caused by plasmin together with other proteolytic enzymes (see Danø et al., 1988, 1990, Grondal-Hansen et al., 1988, Andreasen et al, 1990).

Immunocytochemical studies have suggested that in the invasive areas of tumors, u-PA is located at the membrane of the tumor cells (Skriver et al., 1984), and recent findings indicate that at cell surfaces, u-PA is generally bound to a specific receptor and that this localization may be crucial for the regulation of u-PA catalyzed plasminogen activation in time and space (see Blasi et al., 1987, Danø et al, 1990).

Surface Receptor for U-PA

The cellular receptor for u-PA (u-PAR) was originally identified in blood monocytes and in the monocyte-like U937 cell line (Vassalli et al., 1985), and its presence has been demonstrated on a variety of cultured cells, including several types of malignant cells, human fibroblasts, and also in human breast carcinoma tissue. The receptor binds active 54 kD u-PA, its one-polypeptide chain proenzyme, pro-u-PA, as well as 54 kD u-PA inhibited by the active site reagent DFP, but shows no binding of the low molecular weight (33 kD) form of active u-PA (Vassalli et al., 1985; Cubellis et al., 1986). Thus, binding to the receptor does not require the catalytic site of u-PA, and in agreement with these findings, the binding determinant of u-PA has been identified in the amino-terminal part of the enzyme, in a region which in the primary structure is remote from the catalytic site. The receptor binding domain has been established to be located in the 15 kD amino-terminal fragment (ATF, residues 1–135) of the u-PA molecule, more precisely within the cysteine-rich region termed the growth factor region as this region shows homologies to the part of epidermal growth factor (EGF) which is responsible for binding to the EGF receptor. The amino acid residues which appear to be critical for binding are located within the sequence 12–32 (Appella et al., 1987). Synthetic peptides have been constructed that inhibit the binding at very low (100 nM) concentrations. The lack of cross-reactivity between the murine and the human peptides indicates that the binding between u-PA and u-PAR is strongly species specific.

The human u-PA receptor has been purified and characterized (Behrendt et al. 1990) and its full length cDNA has been cloned (Roldan et al, 1990). The cDNA for uPAR encodes a 335 residue polypeptide which after removal of the signal sequence (Roldan et al., 1990) is further truncated during the post-translational removal of a COOH-terminal signal peptide responsible for the addition of a glycolipid membrane anchor (Ploug et al., 1991a). The mature uPAR sequence (residues 1–283) is divided into three cysteine-rich repeats of approximately 90 amino acids covering the entire sequence and it has therefore been proposed that uPAR is composed of three homologous domains (Behrendt et al., 1991, Ploug et al., 1991b).

These internal repeats of uPAR appear to be related to a family of single domain, glycolipid-anchored membrane glycoproteins, which includes the membrane inhibitor of reactive lysis (MIRL/CD59) and the murine Ly-6 antigens (Palfree 1991, Ploug et al., 1991b). Recently, the disulfide bond connectivity of the $NH_2$-terminal domain of uPAR has been solved (Ploug et al., 1993) and has been found to be homologous to that of the non-glycosylated snake venom α-neurotoxins suggesting that the individual UPAR domains adopt the same overall structural topology as these toxins.

The interaction between u-PA and u-PAR is entirely governed by the high receptor-binding affinity of the small epidermal growth-factor like module of uPA. It has been shown previously that the $NH_2$-terminal domain of u-PAR (residues 1–87; domain 1) associates with u-PA since, firstly, a covalently cross-linked adduct between this domain and u-PA can be formed selectively using disuccinimidyl suberate (Behrendt et al., 1991) and secondly, a monoclonal antibody reactive with this domain inhibits uPA binding to cells (Rønne et al., 1991).

WO 92/07083 discloses i.a. a monoclonal antibody (as well as its use as a drug and its use in methods for the targeting of drugs) which strongly inhibits cell surface plasminogen activation, while this activation is not or only slightly affected by three other antibodies. The monoclonal antibody (3R) also efficiently inhibited binding of radiolabelled DFP-treated u-PA on the surface of U937 cells, while no or only slight inhibition was seen with the three. As the binding of the 3R antibody was completely inhibited by pre-treatment with u-PA it was concluded that this antibody bound to an epitope in the u-PA binding domain of u-PAR.

Based upon these findings, it was in WO 92/07083 concluded that inhibition of receptor binding of u-PA is a means of inhibiting some of its physiological functions in relationship to therapeutic prevention of localized proteolytic activity, e.g. invasion and metastasis of cancer cells, inflammatory bowel disease, premalignant colonic adenomas, septic arthritis, osteoarthritis, rheumatoid arthritis (for which a direct involvement of excess u-PA production has been demonstrated), osteoporosis, cholesteatoma, and a number of skin and corneal diseases for which an excess plasminogen activation has been shown to be the pathogenetic cause, such as corneal ulcers, keratitis, epidermolysis bullosa, psoriasis, and pemphigus. Since u-PA receptors are present on several blood cells (neutrophilic granulocytes and monocytes) and endothelial cells, their regulation might also significantly affect intravascular fibrinolytic activity in physiological, pathological and pharmacological conditions. The above-mentioned diseases would be the first targets for a therapy based on administration of substances that block or decrease cell surface plasminogen activation. Because of a role of u-PA in implantation of the fertilized egg, a contraceptive effect is expected of measures that inhibit receptor binding. The therapy and prophylaxis would involve systemic or topical treatment with agents that block or reduce receptor bound plasminogen activator activity.

WO 92/07083 also discloses that the u-PA binding part of u-PAR is located within the first 87 N-terminal amino acids, and the monoclonal antibodies of WO 92/07083 were shown to bind to the ligand binding part of u-PAR.

SUMMARY OF THE INVENTION

It has surprisingly been found by the inventors that contrary to what has previously been believed, the full receptor, not merely the domain 1 of u-PAR (where the binding site is believed to be located) seems to be necessary to in order to obtain high affinity binding to u-PA.

Herein is disclosed that the extrinsic fluorophore 8-anilino-1-naphthalene sulfonate (ANS) binds to a single hydrophobic site exposed on intact u-PAR and that the enhancement of the fluorescence of bound ANS probes the surface expression of a high affinity binding site for u-PA. In addition, we show that chymotrypsin cleavage after $Tyr^{87}$ in u-PAR greatly reduces the affinity towards u-PA and that such cleavages in the linker region between domains I and II of uPAR is parallelled by a concomitant loss of ANS binding. Finally it is demonstrated that monoclonal antibodies against domain 2+3 exhibit a similar effect, namely the inhibition of binding between u-PA and u-PAR.

A further, very surprising fact, is that the monoclonal antibodies according to the invention are capable of inhibiting the interaction between u-PA and u-PAR to an extent of more than 90%, an effect which has never before been observed.

These findings implicate that high affinity binding of u-PA to the receptor is dependent not only on the availability of the presumed binding site in domain 1, but also on whether additional critical interactions are provided.

It is thus a surprising finding by the inventors that it is possible to disturb such additional critical interactions and thereby effectively prevent binding of u-PA to u-PAR exclusively by influencing domain 2 and/or domain 3, exactly the domains not hitherto believed to be involved in the binding.

The above findings strongly indicate that the binding of u-PA to u-PAR is one in which domain 2 and/or domain 3 plays a critical role, and indeed, experiments with certain antibodies which bind exclusively to domain 2 and/or domain 3, have shown that binding of these antibodies to u-PAR completely abolishes the capability of u-PAR to bind to a u-PA binding form of u-PA.

The most plausible explanation of these phenomena is that it is possible to interact with domain 2 and/or 3, or for that matter with any part or subgenus of domain 2 and/or 3, in such a manner that a critical conformation change of the complete u-PAR molecule takes place, resulting in a practically complete loss of the capability of binding between u-PA and u-PAR.

The logical consequences of such a critical conformation change would be
1) that u-PA cannot bind to the u-PAR molecule, and
2) that even u-PA which might previously been bound to the u-PAR molecule will be displaced, as it has no possibility of remaining anchored in the changed conformation.

Such a conformational or other change where u-PA is positively displaced is believed to be the strongest possible way of preventing binding of u-PA to u-PAR and thus to prevent the effects of such binding, including prevention of the localized proteolytic effect. In contrast to a more traditional displacement of u-PA from the receptor wherein an antibody or another agent would have to compete with u-PA for the access to the binding site, a displacement of u-PA could be brought about without the u-PA concentration itself having any effect on the efficacy of the displacement. If the displacing agent was e.g. a drug, it should be possible to administer the said drug at much lower dosages than a drug exerting its effects by competition with u-PA. In other words: u-PA would not be capable of titrating the binding between the displacing agent and u-PAR.

Thus, the present invention provides a extremely efficient method of preventing receptor-binding of u-PA in a relatively simple manner, namely by directly interfering with the elements which are decisive to the amplification of the presumed u-PA binding to domain 1, thereby destroying the possibility of any u-PA binding of a size which could have any practical importance.

In one broad aspect, therefore, the invention relates to a method for counteracting localized proteolytic activity in a mammal, including a human being, comprising administering to the animal an effective amount of at least one antibody which inhibits the binding between u-PA and u-PAR to an extent of at least 90% in an assay comprising incubation of substantially u-PA free U937 cells at a concentration of 100 µl of cells in PBS, 0.1% BSA with 100 µl of the antibody (20 Ag/ml) for 30 minutes at 4° C., addition of 100 µl $^{125}$I-labelled 0.9 nM ATF and incubation for 1 hour with mixing, and washing of the cells 3 times in PBS, 0.1% BSA and determination of bound ATF by gamma counting, and thereby preventing or counteracting binding of a receptor-binding form of u-PA to u-PAR.

In anther broad aspect the invention relates to these novel antibodies.

Thus, the present invention provides an extremely efficient way of preventing or counteracting u-PAR binding of u-PA and thereby preventing the localized proteolytic activity associated therewith, and it must be presumed that the mechanism of action on which the present invention is based will be the one preferred in future.

DETAILED DISCLOSURE OF THE INVENTION

As explained above, the invention relates to an antibody which inhibits the binding between u-PA and u-PAR to an extent of at least 90% in an assay comprising incubation of substantially u-PA free U937 cells at a concentration of 100 µl of cells in PBS, 0.1% BSA with 100 µl of the antibody (20 µg/ml) for 30 minutes at 4° C., addition of 100 µl $^{125}$I-labelled 0.9 nM ATF and incubation for 1 hour with mixing, and washing of the cells 3 times in PBS, 0.1% BSA and determination of bound ATF by gamma counting, or an active fragment or immunological equivalent of said antibody.

It will be appreciated that the invention relates to this antibody in an at least partially purified form.

The inhibition under these conditions may be even more marked, such as at least 92%, 93%, 94%, 95%, 96%, 97%, 98% and even higher.

By the term "antibody" is herein meant a molecule which is produced by a) B-lymphocytes as a response to an immunological challenge, the molecule having the capability of binding (in some cases with high specificity) to the challenging agent, or b) by a transformed cell which contain the genetic information necessary to express the antibody. The term "active fragment" in this context denotes a binding fragment of the molecule, which is also capable of eliciting the same biological effects on the target molecule as is the antibody itself, although in some instances at higher concentrations than the antibody. By the term "immunological equivalent" is meant a novel substance exhibiting substantially the same binding specificity as the antibody, and exerting substantially the same effects on the target molecule as the antibody, although in some instances at higher concentrations than the antibody proper.

It will be understood that the active fragments and immunological equivalents may fail to inhibit u-PA/u-PAR binding at the concentrations of antibody mentioned above. However, as this is a consequence of the active fragments and the immunological equivalents may be smaller molecules than the antibodies proper, it will be appreciated that by the terms "active fragment" and "immunological equivalent" are also meant molecules which bind to the same binding site as an antibody proper and thereby prevent or counteract binding of a receptor-binding form of u-PA to u-PAR and thereby being capable of preventing or counteracting localized proteolytic activity in a mammal, including a human being, if the molecule is administered to the mammal.

Generally, when used in the present application and claims, the term "antibody" is intended to cover both antibodies, active fragments, and immunological equivalents.

In a preferred embodiment the antibody according to the invention exhibits a substantial binding to a fragment of u-PAR in an immunoprecipitation assay (as described example 2 and in Rønne et al., 1991), said fragment being the C-terminal fragment of u-PAR obtained by incubating 750 μg purified soluble u-PAR with 100 ng α-chymotrypsin for 4 h at 37° C. in 1M $NH_4HCO_3$ followed by addition of 1 mM phenylmethylsulfonyl fluoride and subsequent purification of the fragment by size exclusion chromatography and immuno-affinity chromatography. The size exclusion step removes domain 1, and the immunoaffinity step further purifies the heavy fragments of the size exclusion.

This C-terminal fragment is, according to the art, the non-u-PA binding part of the u-PAR molecule and starts at amino acid residue 88 of intact u-PAR (equivalent to domain 2+3). Therefore, antibodies which react with the non-u-PA binding part of the u-PAR molecule comprising its C-terminal part and starting with amino acid residue 88 in the intact u-PAR molecule are interesting aspects of the invention.

By the term "fragment" is meant a part of the mature u-PAR molecule. In fact, soluble u-PAR is also a fragment of u-PAR as the glycolipid anchor has been abolished from the molecule.

By the term "substantial binding" is meant a binding between an antibody and an antigen which is clearly distinguishable from a non-specific interaction between an antibody and another molecule. Under normal circumstances, the person skilled in the art will have no problems in distinguishing a substantial binding from an unspecific interaction, but as a rule of thumb it can be said that the signal in an immunoprecipitation assay should be clearly distinguishable from a negative control.

As is described herein, the antibodies produced by the hybridoma cell lines 1.C8.26A3 and 1.H2.10A3 exhibits the above binding characteristics. It is believed that the reason for their high potency in inhibiting binding between u-PAR and u-PA is that they have been prepared by i.a. using an immunisation scheme where solubilized u-PAR was the immunogenic agent, in contrast to the hitherto known antibody preparations, which were produced using complete u-PAR as the immunogenic agent. It should be noted that antibodies reactive with domain 2+3 have been described in the art (cf. WO 92/0783), but none of these have exhibited the effects disclosed herein.

Therefore, a very interesting aspect of the invention is an antibody according to claim 1 or 2 being obtainable by immunization of an experimental animal with soluble u-PAR lacking the glycolipid anchor of u-PAR and subsequent recovery and purification of the soluble u-PAR.

Accordingly, antibodies which bind to the same epitope(s) on u-PAR as the monoclonal antibodies produced by the hybridoma cell lines 1.H2.10A3 and 1.C3.26A3, stand a high chance of exerting the same effects on u-PA/u-PAR interaction as do the two antibodies. Such antibodies are thus very interesting aspects of the invention.

It is conceivable that the binding site of u-PAR is not exclusively located on domain 1, but rather is a multidomain binding site, which is affected by the binding of the antibodies of the invention. As can be seen from example 1, the removal of domains 2 and 3 reduces the binding capacity of domain 1 considerably. Therefore, antibodies which bind to domain 1 (and/or 2 and/or 3) and thereby affect the functional features of such a possible multidomain binding site, would also have an effect which resembles the effect exerted by the antibodies of the invention.

However, since much experimental evidence up to this day have pointed at domain 1 as the location of the binding site, and as the effects exerted by the antibodies of the invention are so marked even though they bind domain 2+3, it is believed that the powerful inhibiting effects of the antibodies should be ascribed to the fact that these antibodies bind to domain 2+3 and not to domain 1. Therefore, an antibody according to the invention which exhibits no substantial binding to the u-PA binding site of domain I of u-PAR is a preferred embodiment of the invention and it is also preferred that the antibody exhibits no substantial binding to domain I of u-PAR. Of course, antibodies binding to domain 2 and/or 3 of u-PAR are especially preferred.

The antibodies are also capable of inhibiting the binding of 8-anilino-1-naphthalene sulphonate (ANS) to u-PAR (a binding which can be titrated with u-PA) an effect which can be measured by determining the reduction in fluorescence caused by ANS bound to u-PAR as described in the examples. It is believed that this effect is a proof of the antibodies not merely exerting their effects by simple steric hindrance of u-PA reaching its binding site, as ANS is a low molecular compound and thus should not be very sensitive to such steric hindrance. Therefore, antibodies capable of inhibiting ANS binding to u-PAR (and being reactive with domain 2+3 as described herein) will most likely bind in a manner which ensures the powerful inhibition on u-PA/u-PAR interaction.

An antibody, which, when binding to u-PAR, causes a reduction in the binding of 8-anilino-1-naphthalene sulphonate (ANS) to u-PAR corresponding to a reduction in fluorescence, in the ANS assay as defined herein in Example 1 (with correction for background fluorescence), of at least 50%, such as at least 60%, 70%, 80%, 90%, and 95% is therefore a very important aspect of the invention.

It is expected that the effects exerted on domain 2+3 by the antibodies of the invention makes possible the displacement of u-PA already bound to u-PAR, and as discussed above this should lead to the need for much smaller dosages of the antibodies of the invention when administering them to a subject in order to obtain a therapeutic effect.

Therefore, an antibody of the invention is especially interesting if it substantially displaces u-PAR-bound u-PA from u-PAR.

By the term "substantially displaces" is meant that the addition of the antibody to a system comprising u-PAR with u-PA bound thereto, and with substantially no free u-PA will have the effect that a titration with the antibody starting at 0 molecules will at some point lead to the release of u-PA from u-PAR. At reasonably high concentrations ($\geq 1$ mg/ml) of u-PA and u-PAR in the system, an effect will usually be observed when the antibody and u-PA are present in equimolar amounts, but it may be necessary to titrate up to much higher molar ratios of antibody if the concentrations of u-PA and u-PAR are low (<1 mg/ml).

According to the above, an antibody of the invention, which substantially displaces u-PA in a test wherein 1) u-PAR with u-PA bound thereto is provided, 2) the antibody is added thereto, and 3) the extent to which u-PA has been displaced as an effect of the addition of the antibody is assessed, is very interesting.

A further interesting aspect relies on the fact that the above-described preferred binding to domain 2+3 of the antibodies of the invention in its nature will result in non-competitive binding of the antibody to u-PAR. Therefore, a preferred antibody of the invention is one which substantially displaces u-PAR-bound u-PA from u-PAR, and which is substantially not displaced from u-PAR when adding u-PA. Therefore, an antibody in a preferred aspect of the invention will substantially displace u-PA in a test wherein 1) u-PAR with u-PA bound thereto is provided, 2) the antibody is added thereto, and 3) the extent to which u-PA has been displaced as an effect of the addition of the antibody is assessed, and which is substantially not displaced by u-PA in a test wherein 1) u-PAR with the antibody bound thereto is provided, 2) u-PA is added thereto, and 3) the extent to which the antibody has been displaced as an effect of the addition of u-PA is assessed.

Of course, the important parameter in the evaluation of the effect of an antibody of the invention has on the binding of u-PAR to u-PA is the dissociation constant of the u-PA/u-PAR complex (this constant has a value under physiological conditions of less than about 1 nM), meaning that at equimolar concentrations of u-PA and u-PAR almost no free u-PA will be found. An antibody of the invention capable of changing this dissociation constant to a large degree is a very interesting aspect of the invention in that the binding of the antibody to u-PAR changes the capability of u-PAR to bind a u-PAR-binding form of u-PA from the capability of intact u-PAR to a capability corresponding to a dissociation constant, determined at physiological conditions and in the same way, of at least 50 nM, preferably more such as at least 100 nM, such as at the least 200 nM, 500 nM, and 1000 nM.

It will be understood that although two antibodies are disclosed herein which exert the useful inhibition on u-PA/u-PAR interaction, it is highly likely that other binding sites on domain 2+3 exist which, when having an antibody bound thereto, will affect the whole u-PAR molecule in a manner which resembles the manner exerted by the disclosed antibodies.

Thus, antibodies according to the invention which are especially interesting are those which, when binding to u-PAR, exert the same or substantially the same effect with respect to prevention or counteraction of the binding of a u-PAR-binding form of u-PA to u-PAR as does the binding of the monoclonal antibody produced by the cell line 1.H2.10A3 or the monoclonal antibody produced by the cell line 1.C8.26A3. But of course, antibodies of the invention are in a narrow aspect of the invention those which bind to a site to which the monoclonal antibody produced by the cell line 1.H2.10A3 or to which the monoclonal antibody produced by the cell line 1.C8.26A3 binds, or to a site, the binding to which exerts substantially the same effect with respect to prevention of the binding of a u-PAR-binding form of u-PA to u-PAR.

As disclosed in WO 92/0783, certain antibodies against u-PAR have been produced which are capable of recognising certain glycosylation variant of u-PAR, thereby making it possible to recognize e.g. cancer cells, as these express u-PAR with a distinct glycosylation pattern. As u-PAR is a heavily glycosylated protein, it must be assumed that some antibodies of the present invention will exhibit the same capability of distinguishing glycosylation patterns on u-PAR.

Hence, an important aspect of the invention is an antibody capable of selectively binding to a particular glycosylation variant of u-PAR.

By the term "selectively binding" is meant that the antibody is capable of distinguishing between at least two groups of cells expressing glycosylated u-PAR, the one group preferably being malignant cells.

An antibody of the invention is preferably functionally equivalent to the monoclonal antibody produced by the hybridoma cell line 1.C8.26A3 or to the monoclonal antibody produced by the hybridoma cell line 1.H2.10A3, in that it reacts with domain 2 and/or 3 of u-PAR and thereby inhibits a) the binding of pro-u-PA and active u-PA, and b) cell surface plasminogen activation. The last effect is of course the important one in a clinical situation where it is desired to avoid local tissue degradation by plasmin.

In order to isolate further antibodies of the invention, it is pragmatic to perform screening assays in order to find those exerting the same effects as the disclosed antibodies of the invention. An antibody of the invention should in a preferred aspect be capable of competing in binding to u-PAR with the monoclonal antibody produced by the hybridoma cell line 1.C8.26A3 or the monoclonal antibody produced by hybridoma cell line 1.H2.10A3, as such an antibody would most likely bind to the same epitope as do the two disclosed antibodies.

As some of the antibodies of the invention are capable of binding to domain 2+3 of u-PAR it is likely that these antibodies would also be capable of reacting both with free u-PAR and with complexes between u-PA and u-PAR; it will be understood that this effect will be valuable when assessing whether an antibody of the invention will also be capable of displacing bound u-PA from u-PAR.

It goes without saying that the antibodies according to the invention should, when administered to a subject, not cause any adverse effects such as immunological reactions; such antibodies are therefore preferred (cf. the discussion below concerning weak immunogens).

Preferably, monoclonal antibodies (Köhler and Milstein (1975), Nature 156, 495–497) or their derivatives will be used for diagnostic and therapeutic purposes according to the invention, and therefore monoclonal antibodies are especially preferred according to the invention. In this invention, monoclonal antibodies against epitopes on domains 2+3 of u-PAR are provided.

As mentioned above, two such antibodies have been produced by the inventors and these are very important parts of the invention. The antibodies are:

The monoclonal antibody produced by the hybridoma cell line 1.C8.26A3 which was deposited on Jul. 7, 1994 at DSM (Deutsche Sammlung von Mikroorganismen und Zellkulturen GmbH, Mascheroder Weg 1B, Braunschweig, Germany) with the accession number DSM ACC2179 under the terms and conditions of the Budapest Treaty, and The monoclonal antibody produced by the hybridoma cell line 1.H2.10A3 which was deposited on Jul. 7, 1994 at DSM with the accession number DSM ACC2178 under the terms and conditions of the Budapest Treaty.

Of course, also active fragments or immunological equivalents of these antibodies are interesting.

It will be understood that polyclonal antibodies are also included in the invention, as polyclonals can be produced by immunizing with the epitopes to which the monoclonal antibodies of the invention bind.

The disclosed monoclonal antibodies according to the invention are, as mentioned above, potentially useful as therapeutic agents as a result of their effects on u-PA binding to u-PAR. However, as is well-known in the art, even monoclonal antibodies will probably exhibit some unspecific binding to other molecules, the degree of unspecificity being defined as the capability of the antibody according to the invention of binding to proteins other than u-PAR. This unspecific binding must be so little as to ensure that no considerable damage will be caused to healthy cells when the antibodies according to the invention are used for tumour therapy or in vivo diagnosis. Along the same line of reasoning it should be emphasized that antibodies (or immunological equivalents exhibiting an equivalent binding to u-PAR and effect on u-PA binding to u-PAR) should be chosen with a view to being selective for versions of u-PAR which are present on e.g. malignant cells, but not on non-malignant cells (for instance because of differences in the glycosylation pattern of the two types of u-PAR; cf. WO 92/07083).

The antibodies can be used as whole antibodies, fragments thereof (e.g. FV, $(FV)_2$, Fab, Fab', $F(ab)_2$), chimeric, humanized or human antibodies as long as they are binding the protein in a suitable manner. Short-chain antibody fragments containing only the CDR regions or parts thereof conferring the specific binding to the peptide are also suitable, especially if the antibody is a labelled one.

Here the antibodies can be used as a whole for therapy of malignant diseases (Hale et al., Lancet 2 (1988) 1934–1399; Cobbold et al., Prog. Clin. Biol. Res. (1990) 333, 139–151). In another approach, the antibody or part of it is conjugated or translationally fused to a toxin molecule (immunotoxin), thus effecting specific killing of tumour cells (Brinkmann et al., 1991, Proc. Natl. Acad. Sci. USA 88, 8616–8620; Pastan et al. (1991), Cancer Res. 51, 3781–3787; FitzGerald and Pastan (1989), J. Natl. Cancer Inst. 81, 1455–1461). In another preferred embodiment of the invention, bispecific antibodies are used for tumour therapy (Bonino et al. (1992), BFE 9, 719–723), which may be constructed by in vitro reassociation of polypeptide chains, by hybrid hybridoma generation or by construction of diabodies (Holliger et al. (1993), Proc. Natl. Acad. Sci. USA 90, 6444–6448; Holliger and Winter (1993), Current Opin. Biotechnol. 4, 446–449).

In addition, antibodies coupled to radioactive or fluorescent substances are preferred for detection and treatment of tumours, including carcinomas of the respiratory, gastrointestinal and urogenital system as well as ocular and skin cancers (Profio (19889, Proc, Soc. Photoopt. Instr. Eng. 907, 150–156; Jiang et al. (1991), J. Natl. Cancer Inst. 83, 1218–1225).

For prevention of an immune response, it is preferred to use antibodies which resemble as closely as possible antibodies of human origin (Glassy and Dillman (1988), Mol. Biother. 1,7–13). Such antibodies are, for example, chimeric or humanized (CDR-grafted) antibodies. Such antibodies usually are manufactured from a rodent monoclonal antibody (see e.g. for review: Morrison (1992), Annu. Rev. Immunol. 10, 239–265; Winter and Milstein (1991), Nature 349, 293–299). In a specifically preferred embodiment of the invention, tumour specific human antibodies (Borrebaeck et al. (1988), Proc. Natl. Acad. Sci. USA 85, 3995–3999; Borrebaeck (1988), Immunol. Today 9, 355–359) are used for therapeutic purposes. In addition, it is specifically preferred to prepare human Mabs via phage display libraries, as is described, for example, by Griffith et al., EMBO J. 12 (1993) 725–734.

Also the porcine antibodies disclosed in U.S. Pat. No. 4,132,768 have proven to be non-immunogenic or very weakly immunogenic in human beings.

It is specifically preferred to use, for therapeutic purposes, antibodies which impart effector functions (ADCC, CDC) (Bruggemann et al., J. Exp. Med. 166 (1987) 1357–1361).

Particularly preferably, a human isotype IgG 1 antibody is used.

With regard to immunotoxins, it is preferred to couple the antibody according to the invention to a toxin, such as, for example, Pseudomonas exotoxin, Diphtheria toxin or other toxins (FitzGerald and Pastan (1989)). It is also preferred to couple the antibodies to chemotherapeutics, such as, for instance, doxorubicin, or to radioactively labelled substances which have a cytotoxic effect. Accordingly, the antibodies can be coupled to radioactive compounds and thereby function in "targeted radiotherapy"; one example of a radioactive coupling partner is a suitable Technetium isotope.

Conjugates of the antibodies according to the invention, in particular of human antibodies, for in vivo imaging, using, for instance, radioactive or fluorescent substances, are also preferred.

The therapeutic compounds of this invention may be administered parenterally, such as intravascularly, intraperitoneally, subcutaneously, intramuscularily, using forms known in the pharmaceutical art. The active drug components of the present invention are used in liquid, powdered or lyophilized form and may be combined with a suitable diluent or carrier, such as water, a saline, aqueous dextrose, aqueous buffer, and the like. Preservatives may also be added.

Regardless of the route of administration selected, the compounds of the present invention are formulated into pharmaceutically acceptable dosage forms by conventional methods known to those skilled in the art. The compounds may also be formulated using pharmacologically acceptable acid or base addition salts. Moreover, the compounds or their salts may be used in a suitable hydrated form.

Regardless of the route of administration selected, a nontoxic but therapeutically effective quantity of one or more compounds of this invention is employed in any treatment. The dosage regimen for treating is selected in accordance with a variety of factors including the type, age, weight, sex and medical condition of the patient, type of tumour, the route of administration, and the particular compound employed in the treatment. A physician of ordinary skill can readily determine and prescribe the effective amount of the drug required regarding known antibody therapy approaches (Hale (1988), Cobbold (1990)). In so proceeding, the physician could employ relatively low doses at first, and subsequently, increased dose until a maximum response is obtained.

One important use of the monoclonal antibodies according to the invention (as well as immunological equivalents exhibiting the same effects with respect to binding to u-PAR and affecting u-PA/u-PAR interaction) is as tools for screening for other antibodies or fragments or immunological equivalents thereof for their potential inhibition of u-PA/u-PAR interaction and, thus, for their potential anti-invasive and anti-metastatic effect in cancer as well as in other diseases where u-PA/u-PAR interaction is involved.

As mentioned above, screening for antibodies having the same properties as the antibodies of the invention is an important part of the invention. In fact, the methods of screening for antibodies according to the invention are very important parts of the methods for treatment of disorders and illnesses described below, also.

Such screening should be performed in two tempi. First it should be established that the antibody, fragment, or immunological equivalent of interest exhibits a binding to u-PAR which is a binding as described above, i.e. preferably a selective binding to domain 2 and/or 3. Secondly, it should be established that the antibody has an effect on the u-PA/u-PAR interaction.

Thus, interesting antibodies of the invention are those which can be obtained by performing the following steps:

a) providing the antibody (B), b) establishing that the antibody (B) binds u-PAR, c) establishing that the antibody (B) does not bind to the u-PA binding site of domain I of u-PAR, d) establishing that the antibody (B) is capable of substantially displacing u-PA from u-PAR at a number of molecules of antibody (B) of at least 1 molecule and at the most $10^5$ times the number of the total number of u-PA and u-PAR molecules.

It will be appreciated that this is the modus operandi which is described in detail in example 2.

In accordance with the above discussions, the antibodies of the invention should preferably bind in a non-competitive manner with u-PA, and therefore u-PA should be incapable of displacing from the antibody u-PAR at a number of molecules of u-PA of at least 1 molecule and at the most $10^5$ times the number of the total number of antibody (B) molecules and u-PAR molecules.

The antibodies of the invention should, according to the above discussions of the reasons for the beneficial effects of the disclosed antibodies, be antibodies raised against a soluble form of u-PAR, preferably the recombinant form used in the examples. However, it is not inconceivable that some antibodies raised against complete u-PAR will have the same effects, and these are of course also a part of the invention.

Because it is expected that the glycosylation pattern of u-PAR is important it is preferred that the u-PAR used in the assay (as well as in immunization schemes) is a u-PAR molecule produced in a eukaryotic cell, preferably a recombinant one in order to get the soluble form.

However, it is possible that production in prokaryotic cells will be possible, especially if glycosylation of u-PAR proves of minor importance and if a suitable refolding scheme can be provided (the prokaryotically produced protein is found in the cells as inclusion bodies which are very difficult to refold into their proper conformation). Therefore, u-PAR may also be prokaryotically produced.

In the cases were a compound with the desired effects is already known (e.g. one of the monoclonal antibodies disclosed herein) one simply studies the competition of binding to u-PAR between the known antibody and the candidate antibody, fragment, or immunological equivalent.

An antibody (B) according to the invention could thus be obtained by performing the following steps:

a) providing the antibody (B), b) establishing that the antibody (B) is capable of substantially displacing u-PA from u-PAR at a number of molecules of antibody (B) of at least 1 molecule and at the most $10^5$ times the number of the total number of u-PA and u-PAR molecules, c) establishing that the antibody (B) is capable of substantially displacing an antibody (A) according to any of the preceding claims from u-PAR at a number of molecules of antibody (B) of at least 1 molecule and at the most $10^5$ times the number of the total number of antibody (A) molecules and u-PAR molecules.

In accordance with the above discussions of how to find antibodies binding to the same epitope, the above assay can be supplemented with by establishing whether the antibody (B) is displaceable from u-PAR by an antibody (A) of the invention at a number of molecules of antibody (A) of at least 1 molecule and at the most $10^5$ times the number of the total number of antibody (B) molecules and u-PAR molecules, and it can further be tested that the interaction of the antibody (B) with u-PA is non-competitive by establishing that the antibody cannot be displaced from u-PAR by u-PA at a number of molecules of u-PA of at least 1 molecule and at the most $10^5$ times the number of the total number of antibody (B) molecules and u-PAR molecules.

It is preferred that the antibody (A) in such assays is a monoclonal antibody of the invention, preferably the monoclonal antibodies produced by one of the cell lines 1.C8.26A3 and 1.H2.01A3.

When the above-mentioned characteristics of antibody/u-PAR interaction have been established, it will then be necessary to investigate more precisely the effects of the candidate antibody on u-PA/u-PAR interaction.

This can be performed in a screening assay in which the possible inhibition of u-PA/u-PAR interaction by the antibody is determined by adding the antibody to a system comprising immobilized u-PAR and solubilized u-PA, u-PA bound to u-PAR being detected by being labelled or by means of a labelled anti-u-PAn antibody, or adding the antibody to a system comprising immobilized u-PA and solubilized u-PAR, u-PAR bound to u-PA being detected by being labelled or by means of a labelled anti-u-PAR antibody.

As an example of such an assay may be mentioned a very practical screening ELISA using immobilized monoclonal antibodies against u-PAR for catching u-PAR and subsequently measuring u-PA binding to u-PAR and the possible interference of candidate antibodies thereon, receptor-bound u-PA being detected by a labelled anti-u-PAn antibody, the labelling being, e.g., biotin.

When an antibody has been found positive in the above simple and fast screening, it can suitably be further tested in a much more laborious assay in which the possible inhibition of u-PA/u-PAR interaction by the antibody is determined by adding the antibody to a system comprising u-PAR and radio-labelled u-PA or a derivative thereof, cross-linking any u-PAR bound to u-PA and detecting any cross-linked product by SDS PAGE and autoradiography. A positive result in this assay confirms that the antibody does indeed inhibit the u-PA/u-PAR binding.

Normally, the next step will be to subject an antibody which has been found, in the above assay, to positively inhibit u-PA/u-PAR binding, to an assay in which the possible inhibition of binding of u-PA to u-PAR on the surface of cultured cells is determined by adding the antibody to a system comprising radiolabelled u-PA or a derivative thereof and cells carrying u-PAR and detecting any u-PA or derivative binding to u-PAR by gamma counting of the cells. A positive result in this assay shows that the inhibition of u-PA/u-PAR binding found in the previous assays is not an artefact related to the use of solubilized u-PAR, but is indeed also obtained when u-PAR is bound to cell surface, such as it will be in a clinical situation.

The aim of inhibiting the u-PA/u-PAR interaction is to inhibit u-PA enzymatic activity in biological settings. This can be directly tested in an assay in which the possible inhibition of cell surface plasminogen activation by receptor-bound exogenous pro-u-PA is determined by adding the antibody to cells carrying u-PAR and subsequently adding pro-u-PA, followed by measurement of plasmin generation on the cell surface. This situation with exogeneously added u-PA is similar to the situation in some types of cancer, such as, e.g., colon adenocarcinoma, in which cancer cells produce and contain u-PAR while u-PA is produced by adjacent non-malignant cells in the tumour stroma.

In some types of cancer, however, such as, e.g., squamous skin carcinoma, the cancer cells themselves produce both u-PAR and u-PA. In this situation, the inhibition of u-PA/u-PAR interaction will be more difficult than when the two components are produced by different cells. In order to test whether a given antibody will be capable of inhibiting u-PA/u-PAR interaction under these circumstances, an assay is used in which the possible inhibition of cell surface plasminogen activation by receptor-bound endogenous pro-u-PA is determined by incubating cells carrying u-PAR and producing pro-u-PA with the antibody, followed by measurement of plasmin generation on the cell surface.

An inherent problem in studying the effect of antibodies inhibiting u-PA/u-PAR interaction on invasion and metastasis in animal studies is a species-specificity in u-PA/u-PAR interaction. Therefore, antibodies inhibiting u-PA/u-PAR interaction in the human system will not necessarily inhibit u-PA/u-PAR interaction in experimental animals such as the mouse. This problem is further aggravated when monoclonal antibodies are to be used as the antibodies inhibiting u-PA/u-PAR interaction, because mouse monoclonal antibodies against the human u-PAR do not react with mouse u-PAR. Therefore, a system has been developed according to the invention in which invasion and metastasis of human cancer cells inoculated in the nude mouse can be readily measured. Human cancer cells inoculated in conventional nude mice do not regularly invade and metastasize. According to the invention, a substrain of the nude mouse designated nu/nu META/Bom has been identified in which several cancer cell lines invade and metastasize in substantially all cases. Furthermore, according to the invention, the human cancer cells inoculated into the mouse have, prior to their inoculation, been transduced with the lacZ gene which encodes the enzyme β-D-galactosidase. This enzyme will give rise to a blue staining when subjected to the substrate X-gal. Thus, this system makes it possible to obtain a distinct colour difference between the human cancer cells and the mouse's own cells, thereby very considerably facilitating detection and quantitation of invading cells and metastases. In the experiments described in Example 9 in WO 92/0783, cancer cells invading and metastasizing in this mouse model were found to produce both u-PA and u-PAR. Furthermore, it was found that their invasion and metastasis could be almost completely inhibited by administration of a monoclonal antibody against u-PA, inhibiting cell surface plasmin generation. Together with the above finding that inhibition of receptor binding of pro-u-PA also inhibits plasmin generation, this may indicate that antibodies efficiently inhibiting u-PA/u-PAR interaction on cells which produce both u-PA and u-PAR will also inhibit invasion and metastasis in the nude mouse model.

In addition to a model where the mouse is inoculated with human cancer cells producing both u-PA and u-PAR, a number of other models are also interesting, such as a model in which two types of cancer cells, one producing u-PA, the other producing u-PAR, are inoculated and therefore simulate the clinical situation occurring in some types of cancer where the two components are produced in two distinct cell types. In a third interesting version, human cancer cells producing u-PAR are inoculated together with human tumour-infiltrating fibroblasts producing u-PA.

u-PA/u-PAR interaction-inhibiting antibodies found to inhibit invasion and metastasis in these nude mouse models are likely to be anti-invasive anti-metastatic in human cancer types in which u-PA/u-PAR interaction is believed to be crucial to the invasion and metastasis, such as colon adenocarcinoma, ductal mammary carcinoma and squamous skin carcinoma. Such compounds should therefore, after appropriate toxicological studies in animals, be further studied in phase 1 and phase 2 clinical trials, as they are strong candidates to be efficient anti-invasive and anti-metastatic drugs.

It will be understood that the above-referenced ways of screening for antibodies with hitherto unknown u-PA deplacing effects also constitute important uses of the antibodies and antibodies of the invention. Also, the screening assays for identifying such antibodies are important methods according to the invention for identifying and/or selecting antibodies capable affecting u-PA/u-PAR interaction.

An most important aspect of the invention is, of course, a method for preventing or counteracting localized proteolytic activity in a mammal, including a human being, comprising administering to the animal an effective amount of at least one antibody according to the invention, including an active fragment or an immunological equivalent of said antibody as defined above, and thereby preventing or counteracting binding of a receptor-binding form of u-PA to u-PAR.

On the background of the above discussion, it will be understood that this method will be a most valuable contribution to the control of diseases and conditions involving local tissue destruction because of plasmin activity, e.g. neoplastic malignancies.

A more detailed discussion of the therapeutic and prophylactic use of principles which prevent or counteract localized proteolytic activity in a mammal, including a human being, by preventing or counteracting binding of a receptor-binding form of u-PA to u-PAR is found in the above-mentioned WO 90/12091 and WO 92/0783, in which it is also discussed how such principles can be used in the treatment of non-malignant diseases. Among non-malignant diseases or conditions which are related to the conversion of plasminogen to plasmin can be mentioned thrombolytic disorders or diseases involving tissue destruction and/or tissue remodelling, such as rheumatoid arthritis, colitis ulcerosa, psoriasis, wound-healing, atherosclerosis, or post-traumatic arterial stenosis.

Another aspect of the invention is a method for detecting or quantifying u-PAR in a sample, the detection or quantitation being substantially independent of whether the u-PAR has bound u-PA or not, comprising using, as a catching or detecting antibody or both, an antibody according to the invention, including an active fragment thereof. In such method, the principle of which is disclosed in detail in WO 92/0783, the catching antibody may be a polyclonal antibody and the detection antibody a monoclonal antibody, or the catching antibody may be a monoclonal antibody and the detection antibody a polyclonal antibody, or both the catching antibody and the detection antibody are polyclonal antibodies, or both the catching antibody and the detection antibody are monoclonal antibodies. Other details of this aspect of the invention appear from the following:

One embodiment of the invention relates to a method for detecting or quantifying complexes of u-PAR and u-PA in a sample, comprising using, as catching or detecting antibody, an antibody according to the invention together with an antibody which detects bound u-PA or pro-u-PA as detecting or catching antibody, respectively. The catching or detecting antibody may be a polyclonal or monoclonal antibody. The detecting antibody is preferably provided with a detectable label. In particular, the invention relates to a method for immunohistochemical detection of u-PAR in a sample of tissue sections.

A further embodiment of the invention relates to a method for the detection or quantitation of a glycosylation variant of u-PAR in a sample, comprising using, as detecting antibody, an antibody according to the invention which solely or preferentially binds to the variant, in particular a method in which the glycosylation variant of u-PAR is a variant characteristic to a particular type of cancer cell.

The sample used in the methods of the invention may be serum, plasma or urine from a cancer patient or a suspected cancer patient, in particular an extract from a cancer tissue or a suspected cancer tissue. The sample could also be taken from a patient suffering from or suspected to suffer from a non-malignant disease involving tissue destruction, such as rheumatoid arthritis, colitis ulcerosa, or psoriasis. The present invention also relates to a method for the preparation of a diagnostic agent which is capable of targeting the diagnostic to a cell that contains a u-PAR on the surface, comprising binding the diagnostic to an antibody according to the invention. The diagnostic agent may further comprise a radioactively substance, such as Technetium, or an immunotoxic toxic substance and may be useful for diagnosis in a mammal suffering from cancer or suspected to suffer from cancer.

In another aspect, the invention relates to the use of an antibody according to the invention for the preparation of a composition for preventing or counteracting proteolytic activity in a mammal, in particular a human, by inhibiting the activation of plasminogen to plasmin by preventing the binding of a receptor-binding form of u-PA to a u-PAR in the mammal.

A further aspect of the invention is the use of an antibody as disclosed herein, including an active fragment or an immunological equivalent thereof, for diagnosis or prognosis of the disease paroxysmal nocturnal hematoglobinuria by detection of decreased u-PAR concentration on monocytes and granulocytes in a patient, cf., also in this regard, WO 92/0783 and WO 90/12091.

Finally, the antibodies according to the invention are most useful in diagnosis or prognosis of cancer. In such use, they are employed in the same manners as or in manners analogous to the antibodies disclosed in WO 90/12091 and WO 92/0783, and also in this context, reference is made to the detailed disclosure of such uses in WO 90/12091 and WO 92/0783.

BRIEF DESCRIPTION TO DRAWINGS

FIG. 1: Inhibition of binding of $^{125}$I-labelled ATF to U937 cells by varying amounts of intact u-PAR or u-PAR treated with different concentrations of chymotrypsin. U937 cells were incubated with varying concentrations of either intact u-PAR (■) or u-PAR treated with chymotrypsin at molar ratios of 1:10,000 (♦), 1:1,000 (▲) and 1:100 (▼) as described in the legend to FIG. 2. The cells were then incubated with $^{125}$I-labelled ATF and specific ATF binding determined after subtraction of counts not competable by a large excess of intact u-PAR (this non-specific binding never exceeded 10% of the total ATF binding). Mean data from triplicate determinations are shown expressed as a percentage of ATF binding in the absence of added u-PAR.

Figure 2:
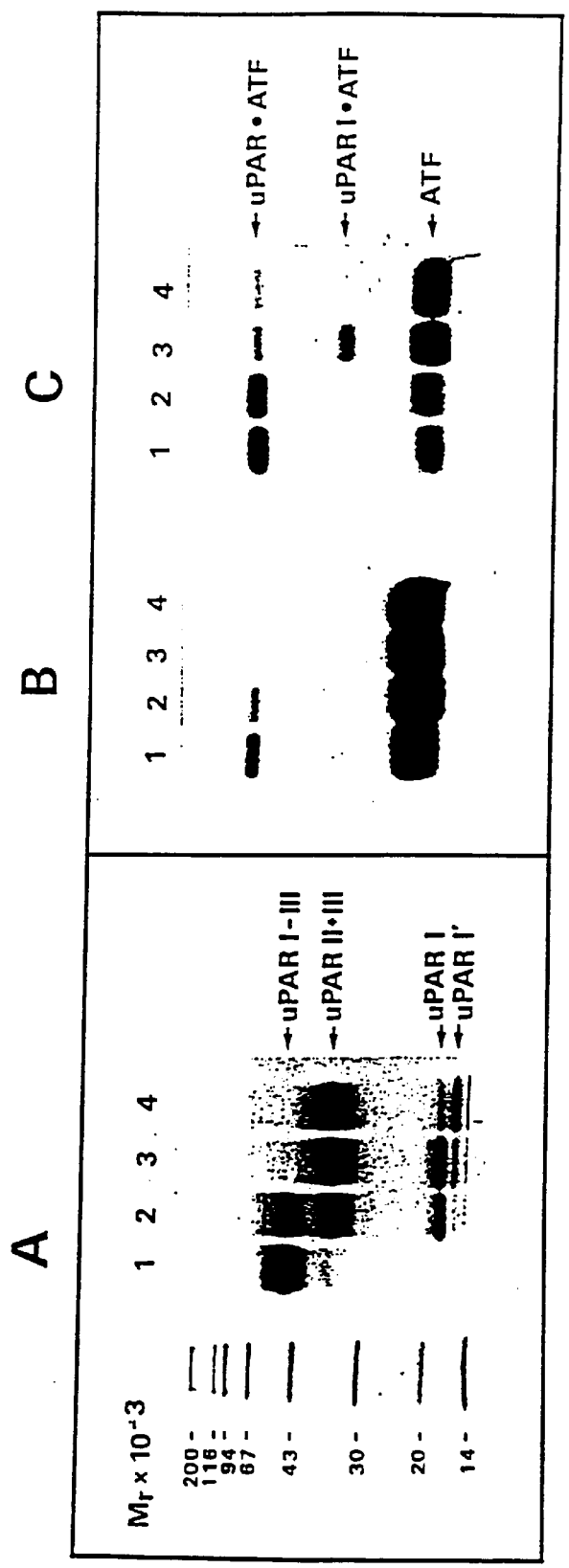

FIG. 2: Ultraviolet absorption difference spectrum of chymotrypsin treated versus intact u-PAR. The UV difference spectrum generated on treatment of u-PAR with a 1:1,000 molar ratio of chymotrypsin for 30 minutes is shown.

Figure 3:
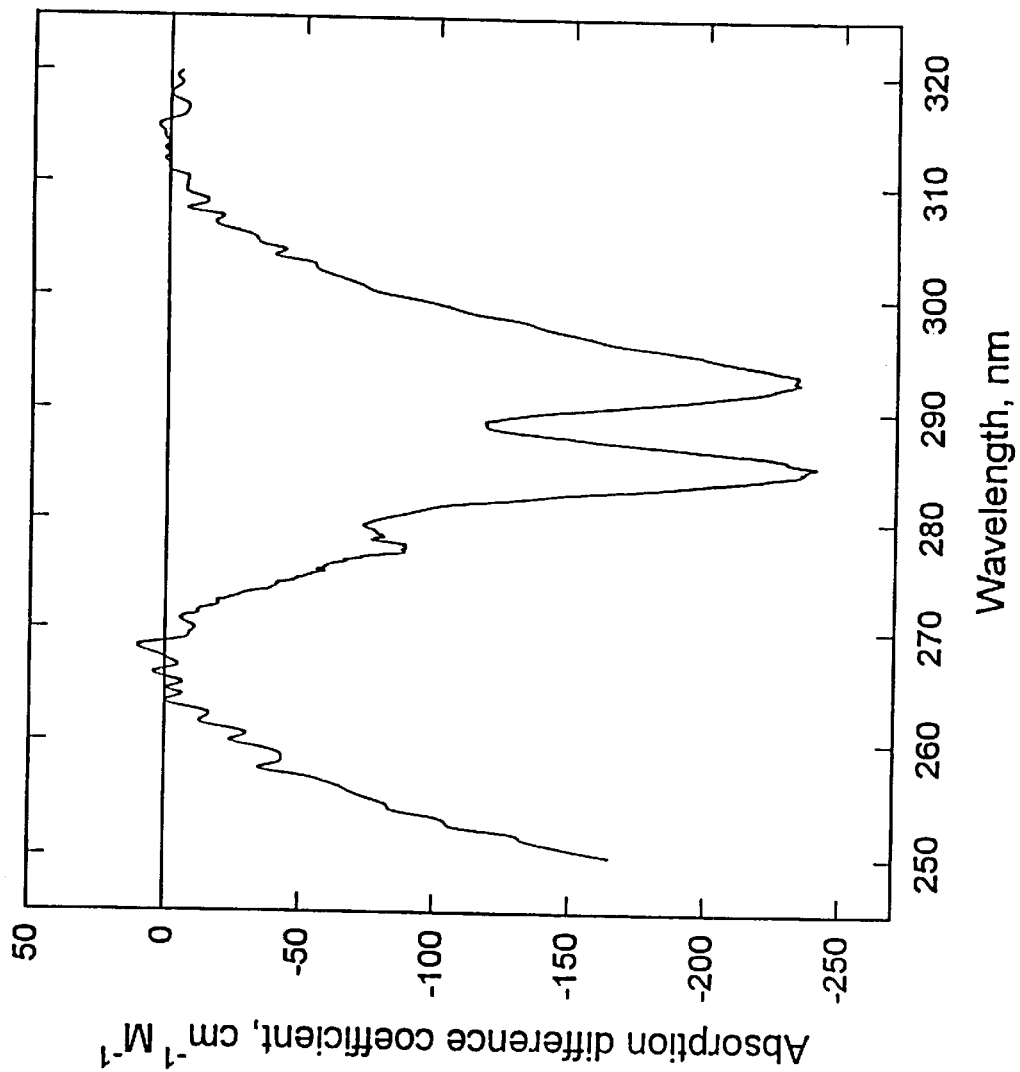

FIG. 3: Fluorescence titration of u-PAR with ANS. Titration of varying concentrations of u-PAR (▲2.5 $\mu$M, ●5.3 $\mu$M, ■10.1 $\mu$M, □68 $\mu$M) with ANS is shown in the main panel. The fluorescence intensities have been corrected for dilution, the background from unbound ANS and inner filter effects as described in "Materials and Methods". The inset shows a Scatchard transformation of these data, from which the stoichiometry and affinity of ANS binding were calculated.

Figure 4:
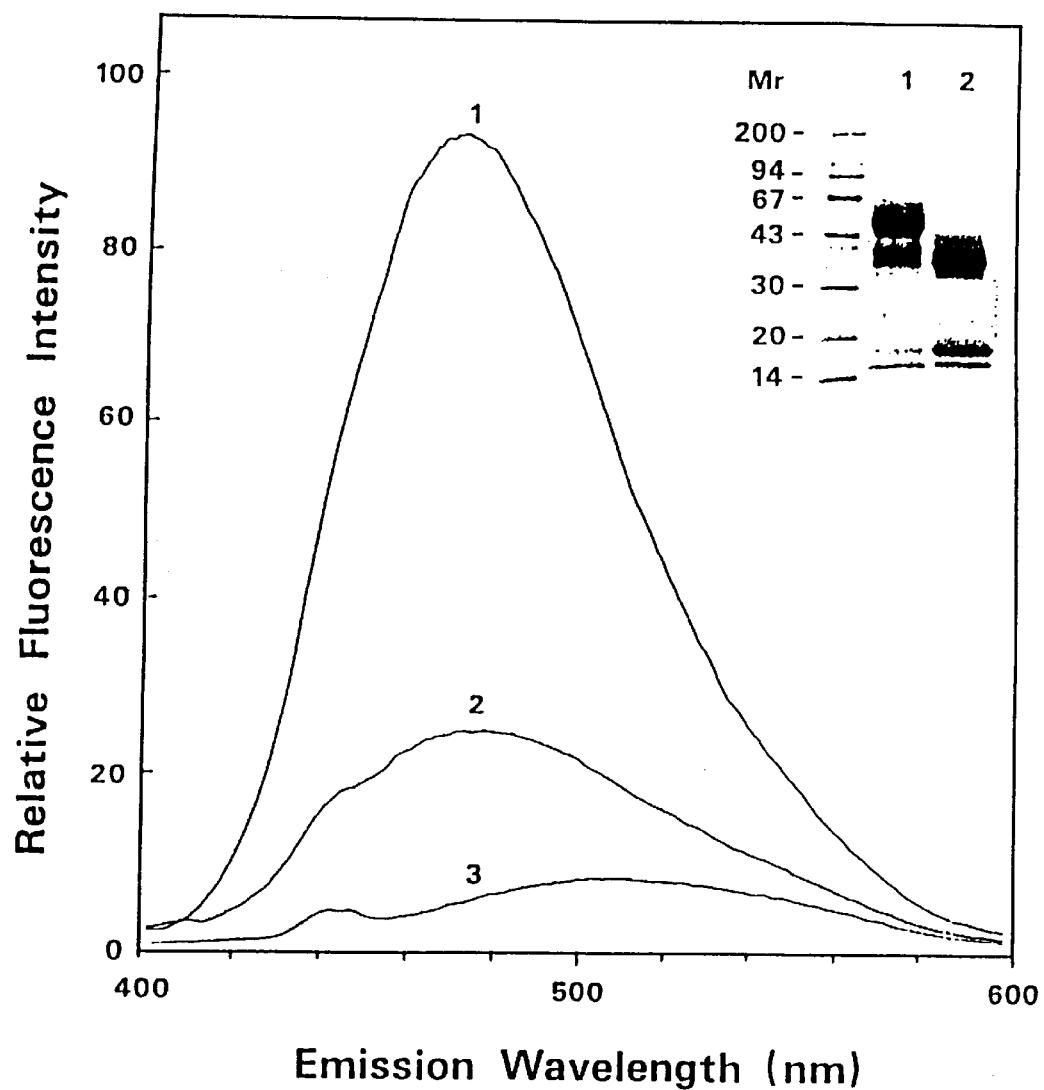

FIG. 4: Interaction between u-PA and u-PAR monitored by ANS fluorescence. The emission spectra of ANS were recorded with 2 $\mu$M u-PAR either alone (curve 1) or in the presence of 2 $\mu$M pro-u-PA, ATF or GFD (curve 2) as well as of 4 $\mu$M GFD (curve 2b) and 8 $\mu$M GFD (curve 2c). Also shown are the spectra for 2 $\mu$M of either ligand alone (curve 3) and of a buffer control (curve 4). The volumes of added ligand never exceeded 10 $\mu$l (2.5% of the total volume).

Figure 5:
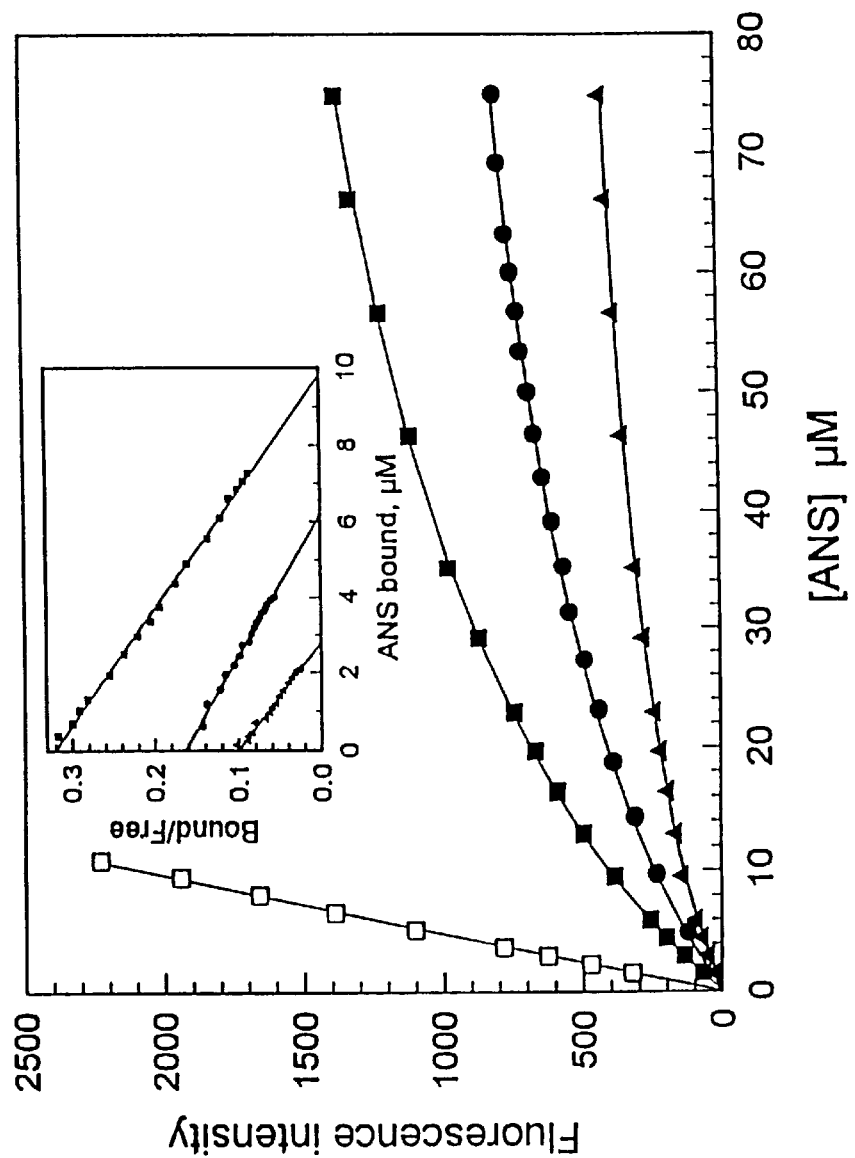

FIG. 5: Titration of the u-PAR dependent ANS-fluorescence by monoclonal antibodies. ANS-fluorescence was measured for 2 $\mu$M u-PAR containing increasing concentrations of 3 different monoclonal antibodies R2 (▼), R3 (■) and R5(●) with excitation and emission wavelengths set at 386 nm and 470 nm, respectively. At the highest concentration of antibody 2 $\mu$M pro-u-PA was added (shown as the respective open symbols). The ANS-profiles shown have been corrected for buffer dilution as well as contribution from intrinsic fluorescence of the individual monoclonal antibodies.

Figure 6:
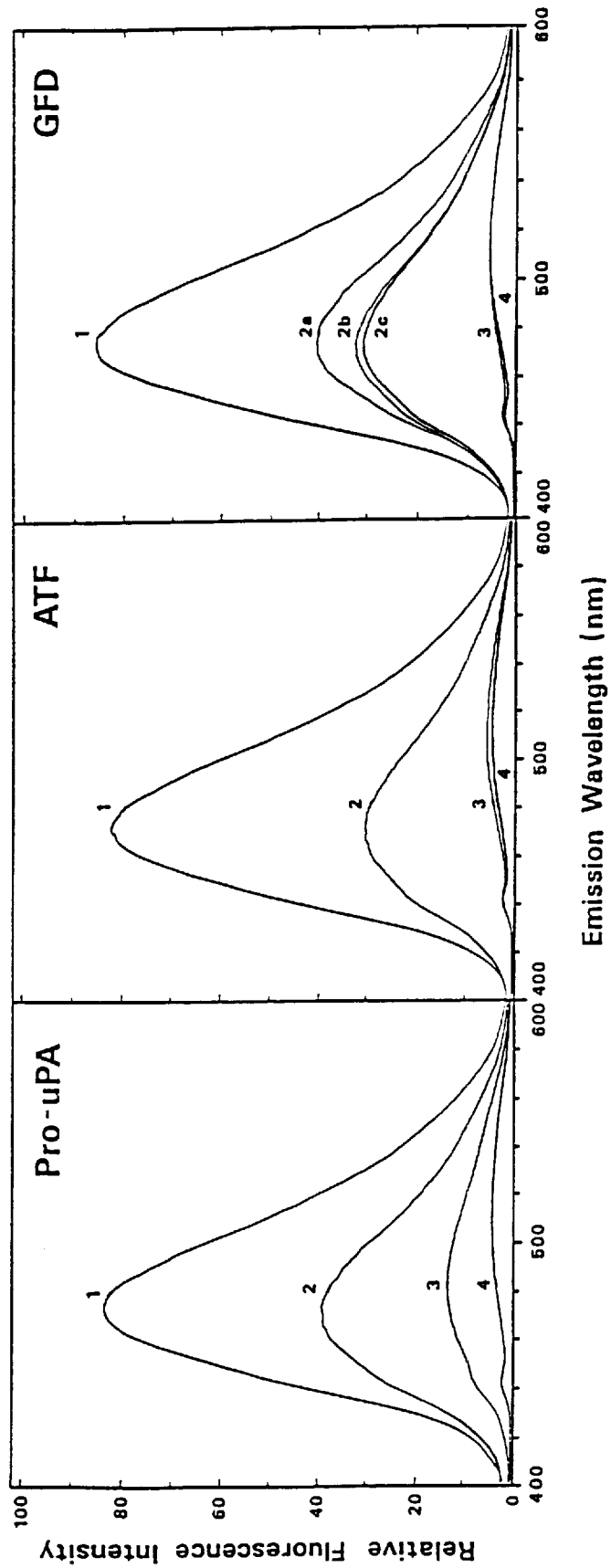

FIG. 6: Guanidine hydrochloride interferes with binding of ANS and pro-u-PA to u-PAR. ANS-fluorescence emission was monitored at 470 nm (excitation at 386 nm) in the presence of 2 $\mu$M u-PAR containing increasing concentrations of guanidine hydrochloride dissolved in 50 mM Tris pH 7.5, 0.1 M NaCl (Δ—Δ). After addition of 2 $\mu$M pro-u-PA the fluorescence was measured again (▲) before the samples were subjected to HPLC gel exclusion chromatography using a Superdex™200 HR10/30 column (Pharmacia) operated at 500 $\mu$l/minutes with the respective guanidine hydrochloride solutions. The fraction of pro-u-PA and u-PAR participating in bimolecular complex formation was calculated from the peak heights corresponding to monomeric and dimeric molecules (●). As monomeric u-PA and u-PAR have almost identical hydrodynamic volumes they coelute during the gel filtration analysis.

EXAMPLES

Example 1

The interaction between u-PA and u-PAR and its proteolytic derivatives.

MATERIALS & METHODS

Chemicals & Reagents. 8-anilino-1-naphthalene sulfonic acid (ANS) was from Sigma (St. Louis, Mo.), stored as a stock solution of 100 mg/ml in water and its molar concentration determined spectrophotometrically using $\epsilon_{386}$=3985 M$^{-1}$ cm$^{-1}$. Guanidine hydrochloride was of ARISTAR® grade from British Drug House (Poole, UK). Phosphate-buffered-saline (PBS) consisted of 10 mM sodium phosphate pH 7.4, 0.15 M NaCl.

Purified proteins. Recombinant pro-u-PA (EC 3.4.21.31) expressed in *Escherichia coli* was a kind gift from Dr. D. Saunders (Grünenthal, Germany). The following purified u-PA derivatives were kindly provided by Drs. A. Mazar and J. Henkin (Abbott, Ill.): The amino-terminal fragment (ATF) of u-PA (residues 6–135), the epidermal growth factor-like module (GFD) of u-PA (residues 4–43), the urokinase kringle (residues 47–135) and low molecular weight u-PA (residues 136–411) containing the serine protease domain (for further details see Mazar et al., 1992). A soluble, truncated u-PAR-derivative (residues 1–277) was purified by immuno-affinity chromatography from the conditioned media of transfected Chinese hamster ovary cells (Ploug et al., 1993) and quantified spectrophotometrically using $E^{1\%}_{280}$ nm=9.2 (Rønne et al., 1994). Monoclonal antibodies to human u-PAR (R2, R3, and R5) were produced and characterized as described previously (Rønne et al., 1991).

Trypsin (EC 3.4.21.4) treated with N-tosyl-L-phenylalanine chloromethyl ketone and α-chymotrypsin (EC 3.4.21.1) were purchased from Worthington (Freehold, N.J.). Human neutrophil elastase (E.C. 3.4.24.27) was from Calbiochem (La Jolla, Calif.) and thermolysin was from Daiwa Kasie (Osaka, Japan).

Generation and purification of u-PAR domain 1 and domain 2+3. Purified u-PAR (750 µg) was incubated with a-chymotrypsin (100 ng) for 4 h at 37° C. in 0.1 M $NH_4HCO_3$ before the digestion was terminated by the addition of 1 mM phenylmethylsulfonyl fluoride. Domain 1 was separated from the remaining intact u-PAR and domain 2+3 by size exclusion chromatography using a Superdex™75 HR 10/30 column (Pharmacia) as described previously (Ploug et al., 1993). This preparation of u-PAR domain 1 was acidified by addition of trifluoroacetic acid and subjected to reversed-phase chromatography on a ProRPC™ HR 5/2 column (Pharmacia) with a linear gradient (1 h) of 0.1% (v/v) trifluoroacetic acid in water to 70 t (v/v) 2-propanol containing 0.085% (v/v) trifluoroacetic acid at a flow rate of 300 µl/minute. This procedure separates u-PAR domain 1 from small quantities of a further truncated derivative.

The fractions from the size exclusion chromatography containing u-PAR domain 2+3 were subjected to immuno-affinity chromatography using an anti-u-PAR monoclonal antibody (R3-recognizing an epitope on domain 1, cf. WO 92/07083) immobilized on N-hydroxysuccinimide activated Superose™ HR 10/2 (Pharmacia) to remove intact u-PAR and domain 1. The runthrough containing domain 2+3 was finally subjected to a second size exclusion chromatography on Superdex™75 after which the descending part of the eluted peak was collected.

Cell-binding experiments. The affinity of u-PA for u-PAR and its proteolytic derivatives was determined in an assay in which the binding of $^{125}$I-labelled ATF to U937 cells was competed by various u-PAR preparations. U937 cells were grown under standard conditions and washed in acidic buffer to remove endogenously bound u-PA as described previously (Ellis et al., 1993). 100 µl aliquots of cells ($1\times10^7$ cells/ml) were resuspended in PBS containing 0.1% bovine serum albumin prior to the addition of 10 µl aliquots of varying dilutions of the u-PAR preparations followed by 10 µl of $^{125}$I-labelled ATF (50 ng/ml and 2.6 µCi/ml). These were incubated for 2 hours at 4° C. with shaking. 100 µl aliquots were then layered on to 200 µl of oil mixture (85:15, v/v of dimethydiphenyl-polysiloxane and ρ=0.88 g/ml mineral oil) in polypropylene microcentrifuge tubes, before centrifugation at 14,000 G for 3 minutes, amputation of the tube tips and γ-radioactivity counting. Specific ATF binding isotherms were then constructed.

Fluorescence measurements. Fluorescence emission spectra of ANS were obtained with a Perkin-Elmer LS-5 spectrofluorimeter using an excitation wavelength of 386 nm and recording emission over the range 400–600 nm, using 5-nm band-pass excitation and emission slits and 5mm path length quartz cuvettes. When the response of the u-PAR-dependent ANS fluorescence was measured as a function of a certain treatment (e.g. proteolysis, titration with monoclonal antibodies or u-PA derivatives) excitation was at 386 nm and emission recorded at a fixed wavelength of 470 nm. All fluorescence measurements were made using 2 µM u-PAR and 10 µM ANS in PBS at 25° C. unless otherwise stated.

ANS titration. The stoichiometry and affinity of ANS binding to u-PAR was determined by titrating fixed concentrations of u-PAR with ANS up to a concentration of 100 µM. The observed fluorescence intensities were corrected for the dilution effect of the added ANS, the low background fluorescence of ANS in buffer and for the inner filter effect of the varying concentration of ANS. The latter was performed using the relationship $$F_{corr}=F_{obs}[(2.303\epsilon_{386}ANS_o)/(1-10^{-\epsilon 386^{ANSo}})],$$

where $\epsilon_{386}$ is the molar extinction coefficient of ANS at half the path length of the fluorescence cuvette, $ANS_o$ is the total ANS concentration, and $F_{obs}$ and $F_{corr}$ are the observed and corrected fluorescence intensities. The concentration of bound ANS was determined from the relationship $$ANS_B=F_{corr}/F_{max},$$

where $F_{max}$ is the theoretical fluorescence of a molar solution if all were bound to u-PAR. This parameter was calculated by titration of a protein concentration sufficiently high to ensure that essentially all added ANS is bound in the initial linear part of the binding curve. The data generated in this way were analyzed by the method of Scatchard.

UV absorption difference spectra. The difference between the ultraviolet absorption spectra of u-PAR before and after limited chymotrypsin degradation was determined using a Beckman DU-70 spectrophotometer. The UV spectrum was recorded digitally at intervals of 0.05 nm for u-PAR at a concentration of 60 µM in PBS at 25° C., prior to the addition of 1/1000 volume of a stock solution of chymotrypsin (60 µM). Additional spectra were recorded until completion of proteolysis, as judged by lack of further spectral changes. Difference spectra were generated by subtraction of the individually recorded spectra. In a control experiment, performed by substituting chymotrypsin with PMSF-treated chymotrypsin under otherwise identical conditions, no absorption difference spectrum was generated.

Miscellaneous analyses. Detection of u-PAR and its functional derivatives was performed by chemical cross-linking using N,N'-disuccinimidyl suberate essentially as described (Nielsen et al., 1988). SDS-PAGE of reduced and alkylated samples was according to Laemnli 1970 and performed in a Bio-Rad Mini-Protean II apparatus.

RESULTS

Chymotrypsin cleavage in the linker region of u-PAR reduces its affinity for u-PA. It has previously been demonstrated that limited chymotrypsin cleavage of u-PAR liberates the $NH_2$-terminal domain (residues 1–87) from the remaining domain 2+3 due to a single cleavage after $Tyr^{87}$ (Behrendt et al., 1991). By chemical cross-linking to $^{125}$I-labelled ATF it was furthermore shown that only the $NH_2$-terminal domain had retained the capability to bind the ligand (Behrendt et al., 1991). The availability of larger amounts of u-PAR protein in the form of recombinant soluble u-PAR (residues 1–277) has allowed us to further investigate the characteristics of this binding. To determine whether the affinity of ligand binding was altered by chymotrypsin treatment, purified recombinant soluble u-PAR (subsequently referred to simply as u-PAR) was subjected to various chymotrypsin concentrations and subsequently tested the degradation mixture in a competitive radiolabelled ligand binding assay, in which the binding of $^{125}$I-labelled ATF to U937 cells was competed by these u-PAR preparations. As shown in FIG. 1, intact u-PAR competed with an IC$_{50}$ of 0.1 nM, which under the experimental conditions used approximates to the K$_d$ of the interaction between u-PAR and ATF. However, with increasing chymotrypsin concentrations there was a large decrease in the affinity of the interaction with the K$_d$ increasing 1,500-fold to 150 nM.

As revealed by SDS-PAGE and Coomassie staining the higher chymotrypsin concentrations led to a complete conversion of intact u-PAR, producing u-PAR domain 2+3 along with u-PAR domain 1 and a further truncated derivative u-PAR I (cleavage after Tyr$^{87}$ and Tyr$^{57}$, respectively). When these samples were subjected to chemical cross-linking to $^{125}$I-labelled ATF they exhibited a decrease in binding activity after chymotrypsin treatment comparable to that observed in the cell binding experiment (FIG. 1). Cross-linking of ATF to u-PAR domain 1 could only be detected using a 100-fold higher concentration of u-PAR (10 nM), consistent with a much reduced affinity. At these high u-PAR concentrations trace amounts of residual intact protein could be detected due to the sensitivity of the method, which possibly contributed to the competitive effect of the chymotrypsin degradation mixture observed above.

In a separate experiment (data not shown), reversed-phase HPLC purified u-PAR domain 1 (residues 1–87) was unable to compete ATF binding to U937 cells even at concentrations as high as 1 μM, despite being able to form a specific covalent complex in cross-linking experiments with an efficiency not distinguishable from that of the degradation mixture. A purified preparation of u-PAR domain 2+3 was able to compete the binding of $^{125}$I-labelled ATF to U937 cells with a K$_d$ of 250 nM, but it cannot be excluded that this was due to trace contamination (<0%) with intact u-PAR, which could be detected (but not quantified) by cross-linking using high concentrations of the preparation.

UV-absorption difference spectrum. To investigate the basis of this very large reduction in ligand binding affinity upon proteolytic liberation of u-PAR domain 1, spectral probes were sought that might reflect differences between intact and partially degraded u-PAR. The UV absorption difference spectrum produced by chymotrypsin treatment of u-PAR is shown in FIG. 2. The UW absorption spectrum of u-PAR is blue shifted by this limited proteolysis due to increased solvent exposure of aromatic residues; the minima at 292 nm and 285 nm indicating net tryptophan exposure while the relative magnitude of the minimum at 285 nm also indicates an additional involvement of tyrosine residue exposure, as does the small minimum at 278 nm (Herskovits, 1967). It should be noted however that these changes are relatively small, and would be accounted for by an approximately 30% increase in solvent exposure of single tryptophan and tyrosine residues.

u-PAR binds 8-anilino-1-naphthalene sulfonate (ANS). Hydrophobic interactions often play a major role in protein-protein interactions and binding of the extrinsic fluorophore ANS to such exposed hydrophobic portions of the protein can be monitored by the accompanying increase in the quantum yield of the fluorescence (Stryer 1965). The ANS binding properties of intact u-PAR was therefore investigated. The intact, u-PAR was indeed found to bind ANS and gave a large enhancement in its fluorescence intensity (>10-fold), together with a blue shift in the emission spectrum from 515 nm to 470 nm; changes which are consistent with ANS binding to u-PAR at hydrophobic site(s) on the protein. Further analysis of the characteristics of this binding revealed that ANS bound to a single site on u-PAR (1.09±0.17 moles/mole u-PAR) with a dissociation constant of 33.8±3.2 μM (FIG. 3). These parameters compare favourably to those of other proteins that specifically bind ANS e.g. complement component C3b binds two molecules of ANS with K$_d$=40 μM (Isenman, 1983), apohemoglobin binds one molecule of ANS per subunit with K$_d$=55 μM (Stryer, 1965).

It was subsequently demonstrated that chymotrypsin cleavage of intact u-PAR led to a 75% reduction in the ANS fluorescence, suggesting either that the specific binding site for ANS had been lost or that the microenvironment of the bound ANS became less hydrophobic causing a lower fluorescence quantum yield. The former possibility is favored by the fact that the wavelength of the fluorescence emission maximum did not change upon chymotrypsin cleavage. Other proteases including trypsin, neutrophil elastase, thermolysin and u-PA that cleave in the linker region between domains I and II of u-PAR caused a similar decrease in the ANS fluorescence intensity.

Titration of receptor-bound ANS by u-PA, ATF and GFD. As both the enhanced ANS fluorescence and the high affinity for u-PA were decreased on chymotrypsin cleavage of u-PAR, it was sought to determine whether the binding of ANS was reporting directly on the integrity of the u-PA binding site of u-PAR. Addition of an equimolar amount of pro-u-PA to a solution of u-PAR caused a reduction in ANS fluorescence equivalent to that obtained upon chymotrypsin cleavage (FIG. 4). The dependence of this effect on the direct interaction between u-PA and u-PAR was demonstrated using smaller derivatives of u-PA. Both ATF and GFD (residues 6–135 and 4–43, respectively) gave a similar reduction in fluorescence to that observed with pro-u-PA (FIG. 4). In contrast, neither the isolated serine protease domain nor the kringle domain (residues 136–411 and 47–135, respectively) had any effect on the ANS fluorescence when added at equimolar concentrations (data not shown). Therefore, the enhancement of ANS fluorescence on binding to u-PAR reflects the availability of a functional, i.e. high affinity, u-PA binding site.

Titration of receptor-bound ANS by monoclonal antibodies. To test whether macromolecular ligands other than u-PA also influence the ANS binding properties of u-PAR the enhanced ANS fluorescence was measured as a function of increasing concentrations of three different anti-u-PAR monoclonal antibodies. FIG. 5 shows that only one of these antibodies, R3, affected the fluorescence, reducing it to a level comparable to that observed after titration with u-PA. The R3 antibody has its epitope on u-PAR domain 1 and has previously been shown to prevent the binding of u-PA; consistent with this, addition of an equimolar amount of u-PA to this u-PAR/R3 mixture caused no further reduction in fluorescence. Therefore this antibody mimics the effect of u-PA on the interaction between ANS and u-PAR. In contrast, ANS fluorescence was not affected by the presence of R2 (recognizing an epitope on domain 2+3). Subsequent addition of u-PA reduced the fluorescence to a level equivalent to that obtained in the absence of the antibody. Addition of the third antibody, R5, recognizing an epitope on domain 1 distinct from that of R3, and that does not block the cellular binding of u-PA (E. Rønne, unpublished data) also had no effect on ANS fluorescence. With this antibody addition of u-PA caused a reduction in the ANS fluorescence approximately 50% of that observed in the presence of R2, possibly due to a minor steric hinderance of u-PA binding in the presence of R5.

Denaturant induced loss of ANS and pro-u-PA binding sites on u-PAR. Exposure of u-PAR to increasing concentrations of guanidine hydrochloride caused a decrease in both the ANS-fluorescence and u-PA-u-PAR complex formation with almost superimposable transition curves having midpoints at 0.8 M guanidine hydrochloride (FIG. 6). No change in the wavelength of the ANS fluorescence emission maximum was observed during the guanidine induced unfolding, suggesting that the observed changes in the ANS fluorescence intensity at 470 nm reflect an equilibrium between molecules which have retained the native structure and those which have lost their ability to bind ANS. A similar equilibrium also exists between monomers and bimolecular u-PA-u-PAR complexes determined by size exclusion chromatography. Addition of equimolar amounts of pro-u-PA to these samples reduced the ANS fluorescence to the same end-level irrespective of the concentration of guanidine hydrochloride.

The unfolding of the ANS and u-PA binding sites of u-PAR occurs at rather low guanidine concentrations (i.e. predenaturational conditions) compared to the transition of the intrinsic tryptophan fluorescence which had its midpoint at 2 M guanidine hydrochloride (data not shown).

Example 2

Inhibition of the upa:upar interaction by monoclonal antibodies against upar domains 2+3
MATERIALS AND METHODS:

Monoclonal antibodies reactive with u-PAR was prepared using a standard immunizing protocol.

For this, soluble, recombinant u-PAR from a CHO culture supernant was purified by affinity chromatography and directly used for the immunization (for details concerning the preparation and purification of soluble, recombinant u-PAR, cf. Ploug et al. (1993), J. Biol. Chem 268, pp. 17539–546, especially page 17540, third paragraph, or Rønne et al. (1994), J. Immun. Meth. 167, pp. 91–101; both these articles are included by reference). For the immunization, sheep, rabbits or mice were used.

50–100 μg u-PAR were given intraperitonally in 0.5 ml Freund's Complete Adjuvant as first immunizing step. This was followed by seven further immunizations (once a month) with 50–100 μg u-PAR in 0.5 ml Freund's Incomplete Adjuvant.

Three days before collecting serum or spleen cells 50–100 μg u-PAR was given i.v. in 100 μl saline.

Spleen cells of the immunized animals were fused with immortal cells, according to the method of Köhler and Milstein (Nature 256 (1975), 495–497).

Immortal cells producing a monoclonal antibody directed against u-PAR were selected from the hybridoma cells obtained in this way and the cells were cloned.

The anti-u-PAR monoclonal antibodies were characterized by immunoprecipitation of chymotrypsin-treated recombinant u-PAR as previously described (Rønne et al, 1991).

Briefly, u-PAR was radio-labelled with $Na^{125}I$ using Iodogen (Pierce Chemicals) according to (Behrendt et al, 1990). 125I-labelled u-PAR was then degraded with chymotrypsin to generate fragments corresponding to domain 1 and domains 2+3 (Behrendt et al, 1991). The monoclonal antibodies at a final concentration of 10 μg/ml were incubated with $^{125}I$-labelled u-PAR fragments (approximately $2 \times 10^4$ cpm) in 200 μl of 0.1 M Tris-HCl, pH 8.1, 0.3 M NaCl, 0.1% BSA, 0.1% CHAPS for 1 hour at 4° C. 50 μl of a 50% suspension of Protein A-Sepharose CL4B (Pharmacia) was added and further incubated for 1 hour at 4° C. with mixing. The Protein A-Sepharose was recovered by centrifugation washed in buffer and then in buffer without BSA. The Sepharose beads were resuspended in 50 μl of SDS-PAGE sample buffer and boiled for 5 minutes and then subjected to 6–16% gradient gels under non-reducing conditions. Immunoprecipitated $^{125}I$-labelled u-PAR fragments were detected by autoradiography.

The ability of the monoclonal antibodies to inhibit the u-PA:u-PAR interaction was assessed in two systems. Firstly, by measuring inhibition of the binding of $^{125}I$-labelled ATF to U937 cells and secondly by measuring the inhibition of the binding of u-PA to immobilized purified recombinant u-PAR.

U937 cells were treated in acidic buffer to remove endogenously bound u-PA (Stopelli et al, 1986). 100 μl of cells in PBS, 0.1w BSA were incubated with 100 μl of monoclonal antibody (20 μg/ml) for 30 minutes at 4° C. 100 μl $^{125}I$-labelled ATF (approximately 0.9 nM) was added and further incubated for 1 hour with mixing. The cells were washed 3 times in PBS, 0% BSA and bound radioactivity determined by gamma counting.

In a further experiment varying concentrations of the antibodies (0.1 to 20 μg/ml) were pre-incubated with the cells to determine the concentration needed for 50% inhibition of $^{125}I$-labelled ATF binding.

The effect of the monoclonal antibodies on the binding of the low molecular weight fluorophore 8-anilino-1-naphthalene sulphonate (ANS) to recombinant u-PAR was assessed for the anti-u-PAR monoclonal antibody R3. Briefly, recombinant u-PAR at a concentration of 2 μM in PBS was incubated with ANS at room temperature in a 5-mm square quartz cuvette and the fluorescence of the ANS recorded in a Perkin-Elmer LS5 spectrofluorimeter at excitation and emission wavelengths of 386 and 470, respectively. The u-PAR solution was then titrated with the monoclonal antibodies, with the ANS fluorescence being recorded after each addition. The inhibition of ANS inding at each concentration of antibody was calculated after the ANS fluorescence had been corrected for buffer dilution and minor contributions to the ANS fluorescence from the antibodies alone. These corrections were made by titrating ANS fluorescence in a solution of u-PAR with buffer alone and by titrating a solution of ANS with the monoclonal antibodies in the absence of u-PAR.
RESULTS:

Monoclonal antibodies 1.C8.26A3 and 1.H2.10A3 (prepared as described above) specifically immunoprecipitated u-PAR do-mains 2+3. The previously characterized anti-u-PAR monoclonal antibodies R2 and R3 (Rønne et al, 1991) were used as controls and immunoprecipitated domains 2+3 and domain 1, respectively. An antibody isotype control (1.F11.21A1) failed to immunoprecipitate either of the u-PAR fragments.

The monoclonal antibodies 1.C8.26A3 and 1.H2.10A3 both inhibited the binding of $^{125}I$-labelled ATF to U937 cells to a degree similar (shown in Table 1) to that of the previously described anti-u-PAR monoclonal antibody R3, which recognizes and immunoprecipitates domain 1 of u-PAR (Rønne et al, 1991). The isotype control antibody 1.F11.21A1 and the previously described antibody R2, which recognizes domains 2+3 of u-PAR (Rønne et al, 1991) had no significant inhibitory effect on binding.

Additional experiments showed that the concentrations of antibody to achieve 50 inhibition of binding were similar for 1.C8.26A3 and 1.H2.10A3, and for R3 (0.6, 0.3 and 0.45 μg/ml, respectively).

The monoclonal antibodies 1.C8.26A3 and 1.H2.10A3 also inhibited the u-PA:u-PAR interaction as determined in a u-PA/u-PAR ELISA system, with a similar concentration dependency as displayed in the radio-ligand cell binding assay described above (cf. Table 2). Monoclonal antibodies 1.C8.26A3 and 1.H2.10A3 were both able to inhibit the enhancement of ANS fluorescence observed on its binding to u-PAR. This enhancement of ANS fluorescence is inhibited by the anti-u-PAR monoclonal antibody R3 and also by u-PA and u-PAR-binding derivatives of it, i.e. ATF and GFD, but not by the monoclonal antibody R2. The enhancement in ANS fluorescence on binding to u-PAR could be abolished by chymotrypsin cleavage of u-PAR, liberating domain 1 from domains 2+3 (cf. example 1). This proteolytic cleavage was also shown to result in a 1500-fold reduction in affinity of u-PA for u-PAR. Therefore ANS binding to u-PAR, monitored as the increase in fluorescence, probes the functional state of the u-PA binding site of u-PAR.

The above data demonstrate that the two monoclonal antibodies 1.C8.26A3 and 1.H2.10A3 bind to domains 2+3 of u-PAR, a part of the u-PAR molecule not previously expected to play any part in the binding of u-PA, and the antibodies thereby inhibit the binding of u-PA or ATF to u-PAR. They also inhibit the binding to u-PAR of the low molecular weight compound ANS, demonstrating that the effect of these antibodies is most probably not due to simple steric hinderance of the macromolecular interaction between u-PAR and u-PA or ATF. The binding of ANS to u-PAR reflects the availability of the high affinity u-PA binding site, which is lost on proteolytic liberation of domain 1. This is most likely due to disruption of inter-domain interactions with in u-PAR, which may act to stabilize the high-affinity conformation of domain 1. Therefore the two monoclonal antibodies 1.C8.26A3 and 1.H2.10A3 inhibit the interaction between u-PA and u-PAR without binding to the known u-PA binding domain 1 of u-PAR, and the observations with ANS suggest that this occurs as a consequence of a change in conformation of the u-PAR molecule, such as to lose its high-affinity u-PA binding site.

TABLE 1

Inhibition of $^{125}$I-labelled ATF binding to U937 cells

|  | c.p.m. (mean of duplicates) | % inhibition of binding |
| --- | --- | --- |
| Binding Control | 6301 | 0% |
| 1.C8.26A3 | 187 | 97% |
| 1.H2.10A3 | 190 | 97% |
| 1.F11.21A1 | 5910 | 6% |
| R3 | 479 | 92% |
| R2 | 9004 | 2% |
| u-PA (Ukidan) | 106 | 98% |

TABLE 2

Inhibition of u-PA:u-PAR interaction determined by u-PA/u-PAR ELISA

| Antibody, µg/ml | % Inhibition | | |
| --- | --- | --- | --- |
|  | 1.H2.10A3 | 1.C8.26A3 | R3 |
| 0.001 | 0 | 2 |  |
| 0.01 | 22 | 10 |  |
| 0.025 | 35 | 14 |  |
| 0.1 | 51 | 35 |  |
| 0.25 | 58 | 53 |  |
| 1.0 | 67 | 65 |  |
| 5.0 | 81 | 75 | 50 |
| 10.0 | 84 | 83 | 61 |

Example 3

Screening for antibodies capable of binding to domain 2+3 and inhibiting interaction between u-PA and u-PAR A number of possible screening assays can be envisaged for the identification of antibodies capable of binding to domain 2+3 and at the same time inhibiting the interaction between u-PA and u-PAR.

Antibodies which bind in an equivalent manner to u-PAR as the antibodies disclosed herein can be identified and selected using a competitive immunoassay in which the antibody which is to be tested compete with a labelled version of e.g. one of the deposited antibodies for immobilized u-PAR.

In this way also other proteinous and non-proteinous antibodies can be tested whether they bind also in an equivalent manner like the deposited antibodies to u-PAR. An equivalent manner means that the antibody to be tested reduces the binding of the labelled antibody to u-PAR by at least 50% in a concentration up to $10^5$ fold higher than the deposited (labelled) antibody when the two antibodies are added simultaneously to a system comprising u-PAR, when compared to the binding between u-PAR and the labelled antibody, when no antibody to be tested is present. The amount of bound labelled antibody can be determined by methods according to the state of the art, e.g. fluorescence of the label or enzymatic reactions catalysed by the label.

When an antibody has been found positive in an assay as the above, the following screenings for the biological effects imposed on u-PAR can be employed:

Substance Screening Scheme

The screening schemes described in example 9 in WO 92/0783 comprises various successive steps which was established to identify substances which can be used to inhibit the interaction between u-PA and u-PAR and thereby be used as drugs to inhibit the invasive and metastatic process. The general strategy described in these assays (having in mind that binding to domain 2+3 is the interesting aspect according to the present invention) can be employed according to this invention, also.

REFERENCES

Behrendt, N., Ploug, M., Patthy, L., Houen, G., Blasi, F., & Danø, K. (1991), J. Biol. Chem. 266, 7842–7847.

Blasi, F. (1988), Fibrinolysis 2, 73–84.

Ellis, V., Pyke, C., Eriksen, J., Solberg, H., & Danø, K. (1992), Ann. N. Y. Acad. Sci. 667, 13–31.

Flemming, T. J., O'hUigen, C., & Malek, T. R. (1993), J. Immunol. 150, 5379–5390.

Fletcher, C. M., Harrison, R. A., Lachmann, P. J., & Neuhaus, D. (1993), Protein Science 2, 2015–2027.

Herskovits, T. T. (1967), Methods in Enzymology 11, 748–775.

Isenman, D. E., Kells, D. I. C., Cooper, N. R., Muller-Eberhard, H. J., & Pangburn, M. K. (1981), Biochemistry 20, 4458–4467.

Isenman, D. E. (1983), J. Biol. Chem. 258, 4238–4244.

Laemmli, U. K. (1970), Nature 227, 680–685.

Mazar, A. P., Buko, A., Petros, A. M., Barnathan, E. S., & Henkin, J. (1992), Fibrinolysis 6, Suppl 1, 49–55.

Nielsen, L. S., Kellerman, G. M., Behrendt, N., Picone, R., Danø, K., & Blasi, F. (1988), J. Biol. Chem. 263, 2358–2363.

Palfree, R. G. E. (1991), Immunol. Today 12, 170–171.

Ploug, M., Rønne, E., Behrendt, N., Jensen, A., Blasi, F., & Danø, K. (1991a), J. Biol. Chem. 266, 1926–1936.

Ploug, M., Behrendt, N., Løber, D., & Danø, K. (1991b), Semin. Thromb. Hemost. 17, 183–193.

Ploug, M., Plesner, T., Rønne, E., Ellis, V., Hoyer-Hansen, G., Hansen, N. E., & Danø, K. (1992), Blood 79, 1447–1455.

Ploug, M., Kjalke, M., Rønne, E., Weidle, U., Høyer-Hansen, G., & Danø, K. (1993), J. Biol. Chem. 268, 17539–17546.

Pyke, C., Kristensen, P., Ralfkier, E., Grøndhal-Hansen, J., Eriksen, J., Blasi, F. & Danø, K. (1991), Am. J. Pathol. 138, 1059–1067.

Roldan, A. L., Cubellis, M. V., Mascucci, M. T., Behrendt, N., Lund, L. R., Danø, K., Appella, E., & Blasi, F. (1990), EMBO J. 9, 467–474.

Rømer, J., Lund, L. R., Eriksen, J., Pyke, C., Kristensen, P., & Danø, K. (1994), J. Invest. Dermatol. (In Press).

Rønne, E., Behrendt, N., Ellis, V., Ploug, M., Danø, K., & Høyer-Hansen, G. (1991), FEBS Lett. 288, 233–236.

Rønne, E., Behrendt, N., Ploug, M., Nielsen, H. J., Wollisch, E., Weidle, U., Danø, K., & Høyer-Hansen, G. (1994), J. Immunol. Methods 167, 91–101.

Stryer, L. (1965), J. Mol. Biol. 13, 482–495.

Vassalli, J.-D., Baccino, D., & Belin, D. (1985), J. Cell Biol. 100, 86–92.

Andreasen P A et al, Endocrinology, 1990, 126: 2567–2576.

Angerer L M, Stoler MH, Angerer RC (1987) In Situ Hybridization with RNA probes: An annotated Recipe. In In situ hybridization. Applications to Neurobiology. Oxford University Press, Oxford, pp. 71–96.

Appella E, Robinson EA, Ullrich SJ, Stoppelli MP, Corti A, Cassani G, Blasi F (1987) The receptor-binding sequence of urokinase. A biological function for the growth-factor module of proteases. J Biol Chem 262: 4437–4440.

Behrendt N et al, 1990, J. Biol. Chem 265: 6453–6460.

Blasi F, Vassalli J-D, Danø K (1987) Urokinase-type plasminogen activator: proenzyme, receptor, and inhibitors. J Cell Biol 104: 801–804.

Cubellis MV, Nolli ML, Cassani G, Blasi F (1986) Binding of single- chain pro-urokinase to the urokinase receptor of human U937 cells. J Biol Chem 261: 15819–15822.

Cubellis MV, Andreasen PA, Ragno P, Mayer M, Danø K, Blasi F (1989) Proc Natl Acad Sci USA 86: 4828–4830.

Danø K, Andreasen PA, Grondahl-Hansen J. Kristensen P, Nielsen LS, Skriver L (1985) Plasminogen activators, tissue degradation and cancer. Adv Cancer Res 44: 139–266.

Danø K, Nielsen LS, Pyke C and Kellermann, GM (1988) Plasminogen activators and neoplasia. In: Tissue-Type Plasminogen Activator (t-PA): Physiological and Clinical Aspects. C. Kluft, ed., CRC Press, Boca Raton. 1988, pp. 19–46.

Danø K et al, 1990, Molecular Biology of the Cardiovascular System, Vol. 132, pp. 173–186.

Grøndahl-Hansen J, Agerlin N, Munkholm-Larsen P, Bach F, Nielsen LS, Dombernowsky P, Daneø K (1988) Sensitive and specific enzyme-linked immunosorbent assay for urokinase-type plasminogen activator and its application to plasma from patients with breast cancer. J Lab Clin Med 111: 42–51.

Roldan AL, Cubellis MV, Masucci MT, Behrendt N, Lund LR, Danø K, Appella E, Blasi F (1990) Cloning and expression of the receptor for human urokinase plasminogen activator, a central molecule in cell surface, plasmin dependent proteolysis. The EMBO Journal 9, 467–474.

Skriver L, Larsson L-I, Kielberg V, Nielsen LS, Andresen PB, Kristensen P, Danø K (1984) Immunocytochemical localization 10 of urokinase-type plasminogen activator in Lewis lung carcinoma. J Cell Biol 99: 753–758.

Vassalli J-D, Baccino D, Belin D (1985) A cellular binding site for the $M_r$ 55,000 form of the human plasminogen activator, urokinase. J Cell Biol 100: 86–92.

We claim:

1. An antibody or an antigen-binding fragment thereof which binds u-PAR at an epitope located outside residues 1–87 of mature u-PAR, and which inhibits the binding between u-PA and u-PAR.

2. The antibody or fragment of claim 1 which binds u-PAR, and which inhibits the binding between u-PA and u-PAR to an extent of at least 90% in an assay comprising
   incubating 100 μl of substantially u-PA free U937 cells in PBS containing 0.1% BSA with 100 μl of the antibody or fragment (20 μg/ml) for 30 minutes at 4° C.,
   adding 100 μl $^{125}$I-labelled 0.9 nM autodigested amino terminal fragment (ATF-uPA) of u-PA, consisting of residues 6–135 of mature u-PA, and incubating for 1 hour with mixing, and
   washing the cells 3 times in PBS containing 0.1% BSA and determining bound ATF-uPA by gamma counting.

3. An antibody according to claim 2, which further exhibits a substantial binding to a fragment of u-PAR in an immunoprecipitation assay, said fragment (residues 88 to end) being the C-terminal fragment of mature u-PAR obtained by incubating 750 μg purified soluble u-PAR with 100 ng α-chymotrypsin for 4 h at 37° C. in 1M $NH_4HCO_3$ followed by addition of 1 mM phenylmethylsulfonyl fluoride and subsequent purification of the fragment by size exclusion chromatography and immuno-affinity chromatography.

4. An antibody according to claim 2, which binds to the same epitope on u-PAR as a monoclonal antibody produced by the hybridoma cell line 1.H2.10A3 which was deposited on Jul. 7, 1994 at Deutsche Sammlung von Mikroorganismen und Zellkulturen (DSM) with accession number DSM ACC2178 under the terms and conditions of the Budapest Treaty, or as a monoclonal antibody produced by a hybridoma cell line 1.C3.26A3 which was deposited on Jul. 7, 1994 at Deutsche Sammlung von Mikroorganismen und Zellkulturen (DSM) with accession number DSM ACC2179 under the terms and conditions of the Budapest Treaty.

5. An antibody according to claim 4, which is a non-competitive inhibitor of the binding of u-PA to u-PAR.

6. An antibody according to claim 2, which is a monoclonal antibody.

7. An antibody according to claim 6, which is the monoclonal antibody produced by the hybridoma cell line 1.C8.26A3 which was deposited on Jul. 7, 1994 at DSM with the accession number DSM ACC2179 under the terms and conditions of the Budapest Treaty, or an active fragment thereof.

8. An antibody according to claim 7, wherein the equivalent is selected from the group consisting of fragments of antibodies, such as FV, $(FV)_2$, Fab, Fab', $F(ab)_2$, chimeric antibodies, humanized or human antibodies, short-chain antibody fragments containing only the CDR regions or parts thereof, and bispecific antibodies.

9. An antibody according to claim 6, which is the monoclonal antibody produced by the hybridoma cell line 1.H2.10A3 which was deposited on Jul. 7, 1994 at DSM with the accession number DSM ACC2178 under the terms and conditions of the Budapest Treaty, or an active fragment thereof.

10. A method for detecting or quantifying u-PAR which comprises forming a complex of u-PAR and the antibody of claim 2, and detecting or quantifying said complex, directly or indirectly, independently of whether the u-PAR has bound any u-PA or not.

11. The antibody or fragment of claim 1 which inhibits uPA-mediated plasminogen activation at the surface of U937 cells.

* * * * *